(12) United States Patent
Chaudhuri

(10) Patent No.: US 8,859,021 B2
(45) Date of Patent: Oct. 14, 2014

(54) SKIN APPEARANCE THROUGH GENE MANIPULATION

(75) Inventor: Ratan K. Chaudhuri, Lincoln Park, NJ (US)

(73) Assignee: Sytheon, Bronton, NJ (US)

( * ) Notice: Subject to any disclaimer, the term of this patent is extended or adjusted under 35 U.S.C. 154(b) by 57 days.

(21) Appl. No.: 12/286,033

(22) Filed: Sep. 26, 2008

(65) Prior Publication Data
US 2009/0036545 A1 Feb. 5, 2009

Related U.S. Application Data

(63) Continuation-in-part of application No. 11/803,188, filed on May 14, 2007, now abandoned, and a continuation-in-part of application No. 11/986,719, filed on Nov. 26, 2007.

(51) Int. Cl.
| | | |
|---|---|---|
| *A61K 36/487* | (2006.01) | |
| *A61K 8/02* | (2006.01) | |
| *A61K 31/05* | (2006.01) | |
| *A61Q 19/08* | (2006.01) | |
| *A23L 1/30* | (2006.01) | |
| *A61K 8/34* | (2006.01) | |

(52) U.S. Cl.
CPC ............... *A61K 8/347* (2013.01); *A61K 31/05* (2013.01); *A61Q 19/08* (2013.01); *A23L 1/3002* (2013.01); *A61K 2800/31* (2013.01)
USPC ............ 424/757; 424/401; 424/776; 514/733

(58) Field of Classification Search
USPC .......................................... 424/757, 776, 424
See application file for complete search history.

(56) References Cited

U.S. PATENT DOCUMENTS

| | | |
|---|---|---|
| 5,716,625 A | 2/1998 | Hahn et al. |
| 6,781,000 B1 | 8/2004 | Wang et al. |
| 7,320,797 B2 | 1/2008 | Gupta |
| 7,351,745 B2 | 4/2008 | Dryer et al. |
| 7,714,026 B2 | 5/2010 | Lin et al. |
| 2006/0251749 A1 | 11/2006 | Jia et al. |
| 2008/0274456 A1 | 11/2008 | Yankner et al. |
| 2008/0286217 A1 | 11/2008 | Chaudhuri |
| 2009/0137534 A1 | 5/2009 | Chaudhuri |
| 2010/0189669 A1 | 7/2010 | Hakozaki |

FOREIGN PATENT DOCUMENTS

| | | | |
|---|---|---|---|
| JP | 11071231 A | | 3/1999 |
| KR | 2000-0007648 | * | 2/2000 |
| KR | 20000007648 A | | 2/2000 |

OTHER PUBLICATIONS

"Cyclooxygenase-2 inhibitor that has Psoraleae extract and/or bakuchiol as its active ingredient and anti-inflammation cosmetics that include Psoraleae extract and/or bakuchiol",Feb. 7, 2000, English translation of KR 2000-0007648, PTO Nov. 1956.*
Poucher's Perfumes, Cosmetics and Soaps, Kluwer Academic Publishers, (10th ed. By Hilda Butler), pp. 403-404.*
Wrinkle and Wrinkle Treatment, www.skin-care-review.com/wrinkle-treatments.html, printed on Feb. 15, 2007.*
The Role of Phytopharmaceuticals in Topical Pain Relief Shyam Gupta Entrepreneur, Dec. 2001.
Interactions between Fibroblasts and Keratinocytes in Morphogenesis of Dermal epidermal Junction in a model of Reconstructed Skin Claire Marionnet, Cecile P Ierrard, Corinne Vioux-Chagnoleau, Julette Sok Daniel Asselineau and Francoise Bernard 2006 the Society for Investigative Dermatology.
Phytologix: ATechnology Platform for Discovering Novel Tyrosinase Inhibitors from Natural Products Qi Jia, Jifu Zhao, Mei Hong, Yuan Zhao, Wenwen MA, Abeysinghe Padmapriya, Terry O'Reilly, Unigen Parmaceuticals Inc. Cosmetic Science Technology 2007.
In Vitro Antimicrobial Activities of Bakuchiol against Oral Microorganisms Harumi Katsura, Ryo-Ichi Tsukiyama, Akiko Suzuki and Makio Kobayashi Antimicrobial Agents and Chemotherapy, Nov. 2001 pp. 309-3013.
Clinically Potential subclasses of Retinoid Synergists Revealed by Gene Expression Profiling Seiichi Ishida, Yukari Shigemoto-Mogami, Hiroyuki Kagechika, Koichi Shudo, Shogo Ozawa, Jun-Ichi Sawada, Yasuo Ohno and Kazuhide Inoue Molecular Cancer Therapeutics vol. 2 49-58 Jan. 2003.

* cited by examiner

*Primary Examiner* — Gina C Justice
(74) *Attorney, Agent, or Firm* — Edward K. Welch, II; IP&L Solutions

(57) ABSTRACT

The present invention relates to a method for treating, preventing and improving the condition and/or aesthetic appearance of aging skin, particularly, treating, preventing, ameliorating, reducing and/or eliminating fine lines and/or wrinkles of skin, through meroterpene induced gene manipulation.

16 Claims, No Drawings

SKIN APPEARANCE THROUGH GENE MANIPULATION

RELATED APPLICATIONS

The present application is a continuation-in-part application of pending U.S. patent application Ser. No. 11/803,188 filed on May 14, 2007 as well as a continuation-in-part application of pending U.S. patent application Ser. No. 11/986,719 filed on Nov. 26, 2007, both of which are hereby incorporated herein by reference in their entirety.

FIELD OF THE INVENTION

The present invention relates to the amelioration, reduction and/or reversal of mammalian skin damage, particularly damage manifesting in the appearance and severity of fine lines and/or wrinkles, through gene manipulation. Specifically, meroterpenes have now been found to markedly affect the expression of certain genes associated with skin health and appearance.

BACKGROUND

Skin is subject to insults by many extrinsic and intrinsic factors. Extrinsic factors include ultraviolet radiation (e.g., from sun exposure), environmental pollution, wind, heat, low humidity, harsh surfactants, abrasives, and the like. Indeed, one of the key elements, if not the primary element, responsible for accelerated skin aging is overexposure to the sun's harmful rays. Intrinsic factors include chronological aging and other biochemical changes from within the skin. Whether extrinsic or intrinsic, these factors result in visible signs of skin aging and environmental damage, such as lines, wrinkling and other forms of surface roughness (including increased pore size, cracking, and flaking) as well as other histological changes associated with skin aging and damage. While extrinsic concerns such as photoaging can be slowed with the use of moisturizers, sunscreens and avoidance of sun exposure, these solutions cannot address the more important and complex causes of skin aging associated with the intrinsic factors. The elimination of lines and wrinkles, combined with a general increased tautness and youthful appearance of skin, has become a booming business in youth-conscious societies. Treatments range from cosmetic creams and specialized moisturizers to various forms of cosmetic surgery.

Perhaps the key underlying physiological change in aging skin is a thinning and general degradation of the skin, most notably a degradation and/or loss of various cells and/or chemical constituents necessary for maintaining the physiological characteristics of youthful skin. Specifically, as the skin naturally ages, the division rate of skin cells slows down causing an overall reduction in the number of cells and blood vessels that supply nutrients and other necessary building blocks for the skin and resulting in a significant decrease in the thickness of the epidermis. Concurrently, as the skin ages proteins, especially collagen and elastin fibers in the underlying layers of skin which provide the scaffolding for the surface layers, begin to weaken and deteriorate and/or manifest a deterioration in their cross-linking capabilities causing the skin to lose elasticity as well as resulting in a flattening of and concurrent loss of mechanical properties, including strength and flexibility, particularly, but not exclusively, in the dermal-epidermal junction (Neerken S, Lucassen G W, Bischop M A, Lenderink E, Nuijs T A, J Biomed Opt. 2004 March-April; 9(2):274-81 and Oikarinen, "The Aging of Skin: Chronoaging Versus Photoaging," Photodermatol. Photoimmunol. Photomed., vol. 7, pp. 3-4, 1990, both of which are incorporated by reference herein in their entirety).

The dermal-epidermal junction (DEJ) is a critical component of the skin and is composed of a network of structural proteins that provide a firm connection between the basal keratinocytes of the epidermis and the dermis. This structural network is made up of (1) the hemidesmosome-anchoring filament complex; (2) the basement membrane comprising two layers, the lamina lucida and the lamin densa, and (3) anchoring fibrils. The lamina lucida is a thinner layer and lies directly beneath the epidermal layer of basal keratinocytes. The thicker lamina densa is in direct contact with the underlying dermis. The basal keratinocytes are connected to the basement membrane via the hemidesmosome-anchoring complex and the basement membrane, in turn, is connected to the dermis via the anchoring fibrils. Each of these components of the DEJ has specific constituents, most notably laminins, integrins tenascin, and above all collagens, specifically collagen IV, and a very precise role to play (Allen J., Br. J. Dermatol. 1997 December; 137 (6): 907-15), (M. Aumailley, Kidney Internat., Vol 47, Suppl. 49 (1995), pp S-4-S-7). Concurrently, these structures are the target of immunologic injury in bullous pemphigoid and epidermolysis bullosa.

The upper surface of the dermis is characterized by dermal papillae containing a plexus of capillaries and lymphatics extending from the papillary dermis perpendicular to the skin surface. These fingerlike projections are surrounded by similar, opposing projections of the epidermis extending from the basal keratinocytes in an interdigitate orientation. Intermediate these fingerlike projections is the dermal epidermal junction layer which, consequently, takes on an undulating character. This highly irregular junction greatly increases the surface area over which the exchange of oxygen, nutrients, and waste products occurs between the dermis and the avascular epidermis. Concurrently, this undulating characteristic combined with the aforementioned anchoring structures ensure cohesion between the dermis and epidermis and accommodates the mechanical deformation of the skin, e.g., as the skin is pulled and stretched, the DEJ will flatten out without loss of cohesion and then return to its normal state as the tension pulling the skin is released. For all these reasons, the DEJ has a very important role to play from a metabolic and mechanical standpoint for the good health of the skin. However, as the skin ages, the quality of the DEJ tends to diminish, most notably as manifested by a flattening of the DEJ, whereby its "undulating shape" drops dramatically, reducing the surface area interchange as well as the elasticity in the skin. (B. Le Varlet et al. Journal of Investigative Dermatology Symposium Proceedings 3: 172-179, 1998). A reduced surface interchange results in a progressive loss of nutrients to the DEJ and the epidermis which, in turn, slows the circulation of the messengers that serve to promote the neo-synthesis process of collagen. Without an optimal amount of collagen, the skin sags even more, propagating the dearth of nutrients. Paradoxically, matured aging skin contains more elastin, which the body uses to fill in the empty space left by the deficiency of collagen. Such elastin is fragmented, calcified, and contains excessive lipids. In addition to the loss of skin thickness due to the lack of collagen support, the aging or aged skin is looser and lacks elasticity. These two properties are the hallmarks of wrinkles and creases.

The important role of the DEJ is also applicable to metabolic diseases when one of the components of the DEJ is absent or of poor quality. For example, bullous pemphigoid is characterized by the absence of laminin-5 which deficiency leads to a detachment of the epidermis from the dermis and the resultant formation of blisters which develop into sores that are difficult to heal. Similarly, psoriasis has been shown to involve molecular and structural alterations of the DEJ arising from an adverse impact on the cytomorphological processes and the normal functions of the basement membrane (Vaccaro M, Pergolizi S, Mondello R, Santoro G, Cannavo S P, Guarneri B, Magauddal L, Archives of Dermatological research, 291(7-8):396-399, 1999).

Numerous efforts have been undertaken for improving the dermal-epidermal junction resulting in a number of successful, at least to some extent, techniques having been developed. Representative disclosures in this area include:

- Marionnet et. al. have shown the utility of vitamin C in improving the DEJ formation in an in vitro human reconstructed skin model leading to a DEJ structure closer to that of normal young looking human skin (Marionnet C, Vioux-Chagnoleau C, Pierrard C, Sok J, Asselineau D, Bernerd F, Meeting abstracts, 34$^{th}$ Annual European Society for dermatological Research Meeting, September 2004, Vinenna, Austria).
- Fisher et. al. have shown an improvement in the DEJ formation and extracellular matrix proteins arising from retinoids (Fischer G J and Voorhees J J, Molecular mechanisms of retinoid actions in skin. FASEB J. 10, 1002-1013 (1996).
- Varani et. al. have shown vitamin A as antagonizing decreased cell growth and elevated collagen-degrading matrix metalloproteases while concurrently stimulating collagen accumulation in naturally aged human skin, Varani J, et. al., J Investigative Dermatology, 114:480-486, 2000).

Numerous investigations have shown the beneficial impact of topical applications of retinoids on skin appearance as well as on various histological parameters such as a thickening of the epidermis including the stratum granulosum, an increase in the height of epidermal ridges or retes of the DEJ and the number of dermal papillae, a gradual displacement of age-related deposition of dermal elastin by collagen and peptidoaminoglycans, normalization of melanocyte function and an increase in the number of dermal fibroblasts. See, for example, Kligman, U.S. Pat. Nos. 4,603,146 and 4,877,805; Zelickson, A. S., J. Cutaneous Aging Cosmet. Dermatol., 1:4147 (1988); Weiss, J. S., JAMA, 259:527-532 (1988); J. Bhawan, Arch. Dermatol., 127:666-672 (1991); and Kligman, L. H., Connect. Tissue Res., 12:139-150 (1984).

- Dyer et. al. (U.S. Pat. No. 7,351,745) teach a method of applying a physiologically effective amount of an active agent, wherein said active agent is S-Methyl-L-Cysteine and S-Phenyl-L-Cysteine in a dermatologically pharmaceutically or physiologically acceptable vehicle, sufficient to increase expression levels of at least one gene selected from the group consisting of: Beta-catenin, Collagen 4, Collagen 7, Frizzled 10, Estrogen Receptor alpha, Hyaluronic acid synthase, and combinations thereof and for improving the condition and appearance of skin.
- Bernerd (US Patent Application: 2004/0005342) teaches the use of ascorbic acid or an analogue thereof in a pharmaceutically or cosmetically acceptable medium, to increase the synthesis of tenascin and/or collagen VII for reinforcing the cohesion at the DEJ.
- Dal Farra et. al. (U.S. Pat. No. 7,211,269) teach a method for preparing cosmetic or dermatological compositions of a sufficient amount of peptides of sequence (Gly-Pro-Gln)$_n$-NH$_2$, wherein: n ranges between 1 and 3, and wherein the amino acids can be in the form L, D or DL, the compositions being designed to promote adhesion between skin cells, promote cell adhesion, to provide curative and/or preventive treatment for aging skin symptoms (of physiological or solar origin) and to enhance skin appearance. In a preferred embodiment, the peptide is of sequence (Gly-Pro-Gln)$_2$-NH$_2$.
- Bonte et. al. (U.S. Pat. No. 6,641,848) teach the use of saponins or sapogenols, particularly those extracted from plants such as soya or Medicago, in cosmetology and for the manufacture of pharmaceutical compositions for treating the skin in order to increase the amount of collagen IV in the dermal-epidermal junction.
- Paufique (U.S. Pat. No. 6,531,132) describes a process for extracting an active principle from yeast whereby the active principle is used to retard the degradation of the dermal-epidermal junction to improve the surface condition of the skin.
- Dumas et. al. (U.S. Pat. No. 6,495,147) describes the use of D-xylene, esters thereof or oligosaccharides containing D-xylose for stimulating the synthesis and/or secretion of proteoglycans and/or glycosaminoglycans by the keratinocytes of a human in need thereof.
- Bonte et. al. (U.S. Pat. No. 6,471,972) teaches a cosmetic treatment method for fighting against skin aging effects wherein the method comprises the application of at least one agent for promoting the adhesion of the keratinocytes of the epidermal basal layer to the dermal-epidermal junction, especially to the collagen IV of said junction, such as, in particular, a divalent metal salt or complex, preferably magnesium aspartate or magnesium chloride, optionally in association with a stimulant of collagen IV synthesis and/or a stimulant of collagen VII synthesis.
- LeSquer et. al. (WO 2002/015869) described combinations of ursolic acid and/or oleanolic acid with a specific palmitoyl pentapeptide Lys-Thr-Thr-Lys-Ser as synergistically increasing/stimulating the neosynthesis of compounds of the DEJ including collagen IV.

Despite all the efforts that have been undertaken to formulate effective compositions for improving the dermal-epidermal junction, current products are not entirely effective. Vitamin C and some of its derivatives are not photochemically or hydrolytically stable. In certain environments, especially in the presence of iron and hydrogen peroxide, Vitamin C can act as a pro-oxidant. Retinoids are very effective, but they also suffer from stability problems. Additionally, retinoids can also cause skin irritation, sensitization and are teratogenic. Plant extracts, if not standardized against key actives, oftentimes are not effective. Peptides are effective, but not fully characterized as yet. For example, though not manifest in short term use, some minor peptide impurities may cause adverse effects over long-term use. Consequently, the user oftentimes finds themselves with no results or an undesired result, e.g., irritation, sensitization, burning sensation, erythema, etc. of the skin.

Alternative approaches to improving the condition or appearance of aging skin that have received increasing attention involve the modulation of extracellular matrix proteins and matrix degrading enzymes and transcription factors. Representative disclosures in this area include:

- Mancini A, Di Battista J A, "Transcriptional regulation of matrix metalloprotease gene expression in health and disease", Front Biosci, 11:423-446, 2006.
- S Reitamo, A Remitz, K Tamai, and J Uitto, "Interleukin-10 modulates type I collagen and matrix metalloprotease gene expression in cultured human skin fibroblasts", Cin Invest, 1994, 94(6):2489-2492, 1994 von Marcschall Z, Riecken E O, Rosewicz S, "Induction of matrix metalloprotease-1 gene expression by retinoic acid in the human pancreatic tumour cell line Dan-G", Br J Cancer, 80(7):935-939, 1999.

Bair E L, Massey C P, Tran N L, Borchers A H, Heimark R L, Cress A E, Bowden G T, "Integrin- and cadherin-mediated induction of the matrix metalloprotease matrilysin in cocultures of malignant oral squamous cell carcinoma cells and dermal fibroblasts", Exp Cell Res, 270(2):259-267, 2001.

Nagahara S, Matsuda T, "Cell-substrate and cell-cell interactions differently regulate cytoskeletal and extracellular matrix protein gene expression", J Biomed Mater Res, 32(4):677-86, 1996

Smits P, Poumay Y, Karperien M, Tylzanowski P, Wauters J, Huylebroeck D, Ponec M and Merregaert J, "Differentiation-Dependent Alternative Splicing and Expression of the Extracellular Matrix Protein 1 Gene in Human Keratinocytes", J Invest Dermatol, 114:718-724, 2000.

Reunamen N, Westermarck J, Hakkinen L, Holmstrom, Elo I, Eriksson J E, Kahari V M, "Enhancement of fibroblast collagenase (matrix metalloproteinase-1) gene expression by ceramide is mediated by extracellular signal-regulated and stress-activated protein kinase pathways", J Biol Chem, 273(9):5137-45, 1998.

McKay I A, Winyard P, Leigh I M, Bustin S A, "Nuclear transcription factors: potential targets for new modes of intervention in skin disease", Br J Dermatol, 131(5): 591-597, 1994.

Liping Du, Neis M M, Ladd P A, and Keeney D S, "Differentiation-Specific Factors Modulate Epidermal CYP1-4 Gene Expression in Human Skin in Response to retinoic Acid and Classic Aryl Hydrocarbon Receptor Ligands" Journal of Pharmacology And Experimental Therapeutics Fast Forward First published on Sep. 19, 2006; DOI: 10.1124/jpet.106.111724).

Despite these advances, there is still a huge need and demand for, and, in following, a tremendous level of research and development effort being expended for, skin care/treatment compositions that are more effective and more forgiving; especially those that are able to provide anti-aging effects. However, in contrast to early efforts, a more fundamental and comprehensive approach is needed for treating aging skin that is based on the biology of the skin. As noted above, skin aging is a natural phenomenon that occurs over time and is not just a result of wear and tear, but is also the consequence of a continually active genetic program that might be up- or down-regulated resulting in detrimental effects on skin. Again, as noted above, aging results in a flattening of the DEJ, a slow down of the division rate of skin cells, a slow down in the production of collagen, and defective cross-linking of collagen and elastin fibers in the skin, among other adverse consequences. Thus, from a biological standpoint, an effective anti-aging strategy for improving the condition and appearance of skin must include rejuvenation of skin cells at both the epidermal and the dermal layers, increased levels of proteins in the dermal-epidermal junction, up-regulation of cell adhesion molecules, protection of the rejuvenated cells and cellular activity, stimulation of the production of skin matrix proteins, down-regulating transcription factors responsible for adverse effects to skin cells and detection and repairing of DNA damage. Biologically based components such as large molecular weight proteins cannot be used topically as they are unable to cross the skin barrier or orally as they tend to quickly degrade in the presence of proteolytic enzymes. Other compounds, such as the retinoids, while effective, have poor stability and at high levels, especially on a continual basis, can be poisonous, even lethal, and result in other adverse consequences including skin sensitization and irritation. Thus, an effective anti-aging composition must readily penetrate through the skin permeability barrier and/or resist biodegradability when taken orally while also having excellent stability with minimal, if any, adverse toxicological effects when used on a continual basis.

Surprisingly, it has now been found that certain naturally derived compounds, as well as their synthetic counterparts, are effective skin care/treatment compositions providing many, if not most, of the desired attributes of the utopian, or nearly utopian, skin care/treatment composition.

Additionally, according to the present invention there is provided a new and effective method for ameliorating, reducing and/or reversing the adverse consequences of skin aging, as well as certain adverse consequences of extrinsic factors, such as sun damage, through the application of a gene manipulating effective amount of these compounds.

Finally, there is provided a new method for preventing or slowing down the adverse consequences of skin aging through the continual application of a gene manipulating effective amount of these compounds.

SUMMARY OF THE INVENTION

It is an object of the present invention to provide a topical composition having one or more meroterpenes or meroterpene extracts capable of beneficially manipulating the expression of one or more genes associated with the dermatological signs of chronologically-aged, hormonally-aged, and/or photo-aged skin such as fine lines, wrinkles and sagging so as to ameliorate, reduce or reverse their manifestation. In following, it is a particular objective of the present invention to provide such a topical composition that is capable of ameliorating, reducing or reversing such adverse manifestations and other conditions associated with the progressive degradation of the dermal-epidermal junction (DEJ) and of the cell-cell cohesion in the epidermis.

It is also an object of the present invention to provide a method of ameliorating, reducing and/or reversing the manifestation of the dermatological signs of chronologically-aged, hormonally-aged, and/or photo-aged skin such as fine lines, wrinkles and sagging, and/or other conditions associated with the progressive degradation of the dermal-epidermal junction (DEJ) and of the cell-cell cohesion in the epidermis, said method comprising the topical application of a gene manipulating effective amount of a meroterpene or meroterpene extract to the affected skin on at least a daily basis until the condition is improved to the satisfaction of the individual.

It is also an object of the present invention to provide a method of preventing the manifestation of the dermatological signs of chronologically-aged, hormonally-aged, and/or photo-aged skin such as fine lines, wrinkles and sagging, and/or other conditions associated with the progressive degradation of the dermal-epidermal junction (DEJ), the extracellular matrix (ECM), the tight junction, cytoskeleton, and the cell-cell cohesion in the epidermis, said method comprising the topical application of a gene manipulating effective amount of a meroterpene or meroterpene extract to the skin, especially those areas of the skin most susceptible to visual skin damage, on at least a daily basis.

According to the present invention there is also provided a method of ameliorating, reducing and/or reversing and/or of preventing the manifestation of the dermatological signs of chronologically-aged, hormonally-aged, and/or photo-aged skin such as fine lines, wrinkles and sagging, and/or other conditions associated with the progressive degradation of the dermal-epidermal junction (DEJ), extracellular matrix (ECM), tight junction, cytoskeleton, and of the cell-cell cohesion in the epidermis, said method comprising the oral or intra-dermal administration of a gene manipulating effective amount of a meroterpene or meroterpene extract.

The preferred meroterpene or meroterpene extract is that comprising bakuchiol, especially purified bakuchiol, and extracts containing the same, most especially those that are free of or substantially free of furocoumarins. For topical applications the meroterpene is carried in an appropriate pharmaceutically and/or dermatologically acceptable carrier and may be in the form of a liquid, ointment, cream, paste, and the like. Preventative topical treatments may comprise most any common skin treatment or cosmetic composition or base which has incorporated therein the meroterpene in a sufficient concentration such that when the compositions is applied in its traditional amount, the amount of meroterpene delivered to the skin is a gene manipulating effective amount. Oral and intra-dermal solutions will comprise the meroterpene in a pharmaceutically acceptable carrier and is typically a liquid or, in the case of oral administered compositions may be a solid, e.g., a pill or capsule.

DESCRIPTION OF THE INVENTION

As used herein and in the appended claims, the phrase "substantially free of" when used in conjunction with or in relation to the meroterpenes means that the recited compound or component, if present, is present at an inconsequential level, generally less than 0.5%, preferably less than 0.1 wt %, based on the weight of the meroterpene. Similarly, the phrase "dermatologically acceptable carrier" is used herein to refer collectively to cosmetically, dermatologically, physiologically and/or pharmaceutically acceptable carriers, diluents, vehicles and media, as context allows. In the latter regard, for example, a composition that is intended to be injected intradermally or taken orally requires a higher level of acceptability as compared to a conventional cosmetic or topical composition and must employ a pharmaceutically acceptable carrier, diluent, vehicle or medium. Generally speaking, a dermatologically acceptable carrier means that the compositions or components thereof so described are suitable for use in contact with human skin and, as appropriate, other organs, without undue toxicity, incompatibility, instability, irritation, allergic response, and the like. Finally, all publications and patent references, including published patent applications, referenced herein are hereby incorporated herein in their entirety.

Meroterpene

Surprisingly, it has now been found that meroterpenes, in sufficient amounts, are effective manipulators of gene expression and, accordingly, can be employed advantageously to address and counteract many of the adverse consequences of aging and other intrinsic as well as extrinsic factors on skin. In particular, it has now been found that meroterpenes are useful for improving the condition and aesthetic appearance of skin, particularly matured or maturing skin, by any one of the following methods: reducing dermatological signs of chronological aging, photo-aging, hormonal aging and/or actinic aging; preventing and/or reducing the appearance of lines or wrinkles; reducing the noticeability of facial lines and wrinkles, including lines and wrinkles on the cheeks, around the eyes and mouth, on the forehead, between the eyes, etc., marionette lines and, in particular, deep wrinkles and creases; preventing, reducing and/or diminishing the appearance and/or depth of lines, wrinkles and/or creases; improving the appearance of suborbital lines and/or periorbital lines; reducing the appearance of crow's feet; rejuvenating and/or revitalizing skin, particularly aging skin; reducing skin fragility; preventing and/or reversing the loss of glycosaminoglycans and/or collagen; ameliorating the effects of estrogen imbalance; preventing skin atrophy; improving skin tone, radiance, clarity and/or tautness; preventing reducing and/or ameliorating skin sagging; improving skin firmness, plumpness, suppleness and/or softness; improving skin barrier repair and/or function; improving the appearance of skin contours; restoring skin luster and/or brightness; minimizing dermatological signs of fatigue and/or stress; resisting environmental stress; replenishing ingredients in the skin decreased by skin aging and/or hormonal changes, especially menopause; improving communication among skin cells; increasing cell proliferation and/or multiplication; increasing skin cell metabolism decreased by aging and/or hormonal changes; especially menopause; retarding cellular aging; improving procollagen and/or collagen production; improving skin texture and/or promoting retexturization; improving skin moisturization; enhancing skin thickness; increasing skin elasticity and/or resiliency; enhancing exfoliation; improving microcirculation; decreasing and/or preventing cellulite formation; improving the dermal-epidermal junction, especially through the prevention, retardation and/or reversal of the flattening thereof due to aging and other factors; and combinations of the foregoing.

Meroterpenes are terpenes having an aromatic ring and are generally of the following chemical structure (I):

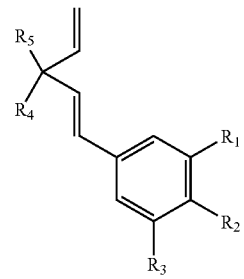

wherein $R_1$, $R_2$, and $R_3$ are each independently selected from the group consisting of H, OH, $OR_6$ or $CH_2R_6$ where $R_6$ is linear or branched $C_1$ to $C_8$ alkyl; and $R_4$ and $R_5$ are each independently a linear or branched, $C_1$ to $C_{20}$ alkyl or alkenyl group. Exemplary meroterpenes include bakuchiol wherein $R_1=R_3=H$; $R_2=OH$, $R_4=CH_3$; $R_5=CH_2CH_2CH=C(CH_3)_2$, corylifolin wherein $R^1=R_3=H$; $R_2=OH$, $R_4=R_5=CH_3$ and hydroxy bakuchiol (having at least one hydroxy group in the aliphatic side chain).

Meroterpenes are typically derived from plants and plant extracts, though they have also been obtained from fungi as well as produced synthetically. Plants and plant extracts, though, remain the most common source of these compounds with *Psoralea corylfolia, Cullen corylifolia, Psoralea grandulosa,* and *Otholobium pubescens* (Fabaceae) being the more common of such plant sources. In the practice of the present invention, the meroterpene may be added as an isolated or purified material of at least 60% purity w/w, preferably at least 95% pure w/w, or it may be added in the form of a purified plant extract containing 1 to about 70% or more by weight meroterpene based on the total weight of the extract. As used herein the phrases "purified plant extract" and "purified extract" means that the extracts are purified to remove coumarins and other deleterious constituents, as discussed below, without specific isolation and recovery of the specific meroterpene and/or multiple fractions are combined or the collection time and temperatures for a given fraction are longer than would be used to isolate a specific meroterpene. Regardless of the nature or form of the meroterpene, the meroterpene is or is most preferably free or substantially free of coumarins, especially furocoumarins like psoralene and iso-psoralene, and other like compounds that are skin sensitizers and/or enhance the detrimental effect of UV exposure. Because such materials are also found in the same plants and extracts, they are typically present in commercial grade meroterpenes and meroterpene extracts. For example, psoralens and iso-psoralens typically comprise 0.1 to 2% of the dry weight of the plant and seed source materials and from 1.0 to 20% by weight of the crude extracts thereof in organic solvents such as ethanol.

The preferred meroterpene for use in the practice of the present invention is bakuchiol. bakuchiol is a known bioactive material and has been used as an anti-tumor agent, an antimicrobial agent, an anti-inflammatory agent, a skin whitening agent, etc. It, in combination with pyridine aldehyde, has also been used in the treatment of pimples, acne, blackheads, herpes, and other skin disorders. However, its use is limited or at least tempered by the presence of high levels of psoralene and other furocoumarins. Although psoralene is a strong bio-active agent, —it is used in combination with UVA for the treatment of psoriasis and eczema—it greatly enhances the sensitivity of skin to the effects of UV exposure, thereby, significantly increasing the potential for sunburn. Consequently, the use of bakuchiol and other meroterpenes, particularly those derived from plant sources, as a treatment has been limited to circumstances where sun exposure is not of concern or where precautions are taken to avoid sun exposure following treatment.

Recent developments, however, have been made in meroterpene production and recovery enabling one to prepare meroterpenes that are free or substantially free of coumarins, especially furocoumarins like psoralene and isopsoralene. For example, Indian patent publication #00570/KOL/2005, (filed Jun. 29, 2005 and published on Jan. 13, 2006) which is incorporated herein by reference in its entirety, describes a method of purifying bakuchiol from the extract of *Psoralea corylifolia* seeds. The method involves extraction of the plant material (powdered seeds) with a non-polar solvent like hexane or heptane. The extract solution is then treated with an alkali solution such as an alkali metal carbonate, bicarbonate or hydroxide to provide a 3-layered volume liquid, an organic layer, an emulsion layer and an aqueous layer. The organic layer is washed with water and dilute HCl and concentrated to a viscous mass. Concurrently, the emulsion layer is dissolved in a polar solvent like ethyl acetate and separated to remove the so-formed aqueous layer. The aforementioned viscous mass is then mixed with the ethyl acetate solution and concentrated to remove ethyl acetate and traces of the non-polar solvent. The concentrated mass is then subjected to high vacuum distillation, generally 1 mm to 0.1 mm at 139° C. to 175° C. That fraction collected between the oil bath temperature of 190-270° C. and vapor temperature range of 140-180° C. is found to contain pure bakuchiol, free or substantially free of psoralene and isopsoralene as well as other known constituents of such plant extracts such bavachicin, bavachin, angelicin, isobavachalcone, bakuchcin, and the like.

A similar method for the preparation of bakuchiol that is free or substantially free of impurities, particularly furocoumarin impurities, is described in Jia et. al. —US 2006/0251749, which is incorporated herein by reference in its entirety. Jia et. al. describes a method wherein the plant source materials are subjected to an extraction and the extract solutions are then subject to hydrolysis with a basic solution such as aqueous sodium hydroxide. The resultant product is then purified by one of column chromatography, extraction followed by crystallization, solvent partition, recrystallization, and combinations of the foregoing. Crude extracts purified in this way are said to be essentially free of furocoumarins such as psoralene and isopsoralene.

Other publications or patents that describe isolation or synthesis of meroterpenes include:

C N Backhouse, C L Delporte, R E Negrete, S Erazo, A Zuniga, A Pinto, B K Cassels, J Ethnopharmacology, 78(1):27-31, 2001.

H Haraguchi, J Inouye, Y Tamara, K Mizutani, Planta Medica, 66(6):569-571, 2000.

J M Krenisky, J Luo, M J Reed, J R Carney, Biol Pharm Bull, 22(10):1137-1140, 1999.

H Katsura, R Tsukiyama, A Suzuki, M Kobayashi, Antimicrobial Agents and Chemotherapy, 45(11):3009-3013, 2001.

S Adhikari, R Joshi, B S Patro, T K Ghanty, G J Chintalwar, A Sharma, S Chaftopadhaya, T Mukherjee, Chem Res Toxicol, 16:1062-1069, 2003.

J B Perales, N F Makino, D L Van Vranken, J Org Chem, 67:6711-6717, 2002, all of which are incorporated herein by reference in their entirety. These purified meroterpenes, especially the purified bakuchiol, may be obtained from Sytheon Ltd., of Lincoln Park, N.J., USA and Unigen Pharmaceuticals, Inc. of Lacey, Wash., USA.

The meroterpene is applied to the skin in a gene manipulating effective amount. Specifically, the meroterpene is applied in an amount that induces at least a two-fold increase or, as appropriate, decrease in gene expression of one or more genes associated with skin health or damage, respectively. Most preferably, the amount applied is that which induces at least a four-fold increase or, as appropriate, decrease in gene expression. Those skilled in the art, especially the pharmacological art, will readily appreciate and apply traditional processes for assessing gene manipulation of the meroterpenes through the determination of their impact on the expression levels of skin related nucleic acid biomarkers. Such assays embrace a variety or methods for measuring nucleic acid levels in cells that have been exposed to one or more test substances. Suitable methods include detection and evaluation of gene activation or expression of, for example, DNA, RNA, or mRNA. As non-limiting examples, polymerase chain reaction (PCR) assays (e.g., RT-PCR), Northern blotting, in situ hybridization, and other assays as known and practiced in the art may be employed to quantify RNAS in cells being assayed for tolerance to a particular treatment (see, e.g., J. O'Connell, 2002, RT-PCR Protocols, Humana Press, Totowa, N.J.; R. Rapley and D. L. Manning, 1998, RNA Isolation and Characterization Protocols, Humana Press; R. Rapley, 2000, Nucleic Acid Protocols Handbook, Humana Press; J. Sambrook et. al. 1989, Molecular Cloning: A Laboratory Manual, Cold Spring Harbor Laboratory, Cold Spring Harbor, N.Y.; R. Higuchi et. al., 1992, Biotechnology, 10:413-417; R. Higuchi et. al., 1993, Biotechnology, 11:1026-1030; E. S. Kawasaki, 1990, "Amplification of RNA", in RNA Protocols: A Guide to Methods & Applications, M. A. Innes, et. al. Academic Press, San Diego, Calif., pp. 21-27; all of which are incorporated herein by reference). Additionally, gene expression in skin, skin substitute or cultured cells may be evaluated using gene (cDNA) arrays (microarrays or nucleic acid genechip test arrays), serial analysis of gene expression (SAGE) or differential display techniques (See e.g., V. E. Velculescu et. al., Science, 270(5235):484-487, 1995; A. Lal et. al., Cancer Res., 59(21):5403-5407; both of which are incorporated herein by reference).

A DNA microarray is a high-throughput technology used in molecular biology and in medicine. It consists of an arrayed series of thousands of microscopic spots of DNA oligonucletoides, called features, each containing pico moles of a specific DNA sequence. This can be a short section of a gene or other DNA element that are used as probes to hybridize a cDNA or cRNA sample (called target) under high-stringency conditions. Probe-target hybridization is usually detected and quantified by fluorecence-based detection of fluorophore-labeled targets to determine relative abundance of nucleic acid sequences in the target. DNA arrays are different from other types of microarray only in that they either measure DNA or use DNA as part of its detection system. DNA microarrays can be used to measure changes in expression levels or to detect single nucleotide polymorphisms. Similarly, in an mRNA or gene expression profiling experiment the expression levels of thousands of genes are simultaneously monitored to study the effects of certain treatments, diseases, and developmental stages on gene expression.

Depending upon the extent of gene expression manifested by the select meroterpene and, as appropriate, the target gene or genes, those skilled in the art, especially the pharmaceutical art, will readily be able to determine the appropriate concentration of the meroterpene to be incorporated into the composition to be applied depending upon the method and form of application or administration as well as the nature of the composition to be applied. For example, a topical ointment may have a higher concentration and a smaller application rate than a sunscreen or cosmetic base formulation that is to be applied at a higher rate, i.e., a greater volume per set surface area. Similarly, an orally administered composition will involve difference concentrations to take account for the dilution and/or degradation in the body of the meroterpene.

As noted above, in accordance with the practice of the present invention, it is necessary to deliver a gene manipulating effective amount of the meroterpene to the skin or targeted skin, particularly those live skin cells of the epidermis and/or dermis that influence skin overall conditioning, characteristics, properties and the like, most especially that influence the dermal-epidermal junction and its function. Exemplary genes that are or should be the target of the gene manipulating meroterpene include, among others, any one or more of the following: integrin beta 4 (ITGB4), integrin beta 6 (ITGB6), Integrin beta-8-precursor (ITGB8), collagen IV (COL4A6), collagen XVII (COL17A1) heparin sulfate glucosamine 3-O-sulfotransferase 1 precursor (HS3ST1), elastase inhibitors (PI3, SERPINB1, ELA3B), proteoglycan, hyaluronan synthase (HAS2, HAS3), claudin 7 (CLDN7) and the like. Other targeted genes for up-regulation and down-regulation include those set forth in the discussion below.

Generally speaking, the meroterpene should be applied or administered so as to provide a dosing of at least about 100 to 250 µg/cm$^2$, preferably at least about 500 µg/cm$^2$, most preferably at least about 1,000 µg/cm$^2$ to skin surface to be treated. The amount should not exceed 10,000 µg/cm$^2$, except, perhaps in the treatment of severe skin conditions. For oral application, a dose/day/adult is about 10 to 500 mg one or twice a day. Still, as with all pharmacological agents, it is best to use only that level of the meroterpene active as is necessary to achieve the desired result without adverse consequences to the individual.

Typically, topical skin treatment compositions and cosmetic products according to the present invention will contain from about 0.001 to about 20, preferably from about 0.1 to about 10, more preferably from about 0.5 to about 5, weight percent of the meroterpene based on the total weight of the skin treatment composition or cosmetic product. Higher levels could be used but are not thought to be necessary. When the meroterpene is added as a purified plant extract or as a purified material that also contains other components, the weight percent is based on the meroterpene content itself.

Dermatologically Acceptable Carrier

The meroterpene active is administered topically, orally or intradermally in a dermatologically acceptable carrier. The carrier is that material or combination of materials that is used to carry or deliver the meroterpene active. For topical applications the carrier can be in a wide variety of forms including, for example, liquids, lotions, creams, masks, toners, serums, gels, foams, emulsions, dispersions, sprays, liposomes, coacervates, ointments, transdermal patches, etc. Accordingly, the carrier may be an aqueous-based solution or cleanser; an alcohol-based solution or gel; an ointment based on fats, waxes, animal and vegetable oils, and solid and liquid hydrocarbons; or an emulsion carrier, including, but not limited to, oil-in-water, water-in-oil, water-in-oil-in-water, and oil-in-water-in-silicone emulsions, etc. The carrier can also be, for example, formulated as alcohol or water based cleansers, toilet bars, liquid soaps, shampoos, bath gels, hair conditioners, hair tonics, pastes or mousses. The carrier will generally comprise from about 30% to about 99.99%, preferably from about 50% to about 99.9%, more preferably from about 80% to about 99%, most preferably from about 85% to about 95% of the skin treatment composition of the present invention based on the combined weight of the actives and the carrier.

Generally speaking, any compatible carrier or base composition employed in traditional cosmetic and/or dermatological applications/compositions as well as pharmacological skin treatment compositions, particularly topically applied pharmacological skin treatment compositions, may be used in the practice of the present invention. Suitable carriers and carrier compositions are described at length in, for example, Gonzalez et. al.—U.S. Pat. No. 7,186,404; Aust et. al.—U.S. Pat. No. 7,175,834; Roseaver et. al.—U.S. Pat. No. 7,172,754; Simoulidis et. al.—U.S. Pat. No. 7,175,835; Mongiat et. al.—U.S. Pat. No. 7,101,536; Maniscalco—U.S. Pat. No. 7,078,022; Forestier et. al. U.S. Pat. Nos. 5,175,340, 5,567,418, 5,538,716, and 5,951,968; Deflandre et. al.—U.S. Pat. No. 5,670,140; Chaudhuri—U.S. Pat. Nos. 7,150,876, 6,831,191, 6,602,515, 7,166,273, 6,936,735, 6,831,191, and 6,699,463; Chaudhuri et. al.—U.S. Pat. Nos. 6,165,450 and 7,150,876; Bonda et. al. U.S. Pat. No. 6,962,692; and Wang et. al. U.S. Pat. No. 5,830,441, all of which are incorporated herein by reference in their entirety. An especially preferred description of suitable dermatologically acceptable carriers and their preparation is set forth in Dryer et. al., U.S. Pat. No. 7,351,745, which is hereby incorporated herein by reference in its entirety.

Obviously, the selection of the carrier and type of carrier depends upon a number of factors including the intended application route for the meroterpene active. For example, a topical composition for daily preventative use may employ a traditional cosmetic base or foundation, a moisturizer cream, a sunscreen composition, and the like for application. Similarly, a topical application to be applied to address a pre-existing skin condition may employ a similar carrier or a carrier more traditional for topically applied pharmaceuticals. Alternatively, the carrier may be in the form of a transdermal patch so that the meroterpene active can be more specifically targeted to the area in need of repair or remediation. Orally or intradermally administered meroterpenes, on the other hand, will employ traditional pharmaceutically acceptable carriers for the mode of application, particularly aqueous and aqueous based solvents or media wherein the meroterpene is dissolved, dispersed, suspended, emulsified, etc. in the solvent or, if a multiphase system, one phase of the system. Alternatively, orally administered compositions will employ various solid adjuvants, excipients and fillers and the resultant composition placed into capsules or formed into pills, tablets, or caplets for ingestion.

In order to enhance and/or expedite the penetration of the meroterpene through the skin layers to, in particular, the targeted basal keratinocytes, the dermal epidermal junction, extracellular matrix, and/or the tight junction, the compositions of the present invention may further include one or more skin penetrants. Skin penetrants are additives that, when applied to the skin, have a direct effect on the permeability of the skin barrier: increasing the speed with which and/or the amount by which certain other compounds are able to penetrate into the skin layers. Exemplary organic penetration enhancers include dimethyl sulfoxide (DMSO); isopropyl myristate; decyl, undecyl or dodecyl alcohol; propylene glycol; polyethylene glycol; $C_{9-11}$, $C_{12-13}$ or $C_{12-15}$ fatty alcohols; azone; alkyl pyrrolidones; diethoxy glycol (Transcutol); lecithin; etc. Surfactants can also be used as penetration enhancers.

For topical applications it is also desirable to formulate the composition so as to be mild and non-irritating to the skin. Accordingly, it is preferable to neutralize the compositions to a pH of from about 3.5 to about 7.0, preferably from about 4.0 to about 6.5, more preferably from about 4.5 and about 6.0. A wide variety of acids, bases, and buffers can be utilized to adjust and/or maintain the pH of the compositions useful in the present invention. Examples of materials useful for adjusting and/or maintaining the pH include, without limitation, ammonia, sodium carbonate, sodium hydroxide, ammonium hydroxide, potassium hydroxide, arginine, triethanolamine, hydrochloric acid, phosphoric acid, sodium hydrogen phosphate, sodium dihydrogen phosphate, citric acid, and the like.

Other optional adjunct ingredients for the skin treatment compositions of the present invention include preservatives, waterproofing agents, fragrances, anti-foam agents, plant extracts (Aloe vera, witch hazel, cucumber, etc), opacifiers, stabilizers, other skin conditioning agents, and the like, each in amounts effective to accomplish their respective functions.

While the topical compositions of the present invention may be formulated for their specific task, namely the remediation, amelioration, repair, reversal and/or prevention of skin damage due to aging and other conditions, it is also advantageous to provide a dual or multi-functional role to the composition. For example, the compositions of the present invention may also serve as skin moisturizers, sunscreens, cosmetics, acne treatments, and the like. This dual or multi-functionality may be accomplished by adding the meroterpene active to conventional skin care and/or treatment products with which they are compatible or by adding conventional components, particularly those regarded as the "active" components, of such other skin care and/or treatment products to the compositions of the present invention. The skilled practitioner will immediately realize and appreciate the versatility offered by the present invention as well as identify a host of other ingredients, excipients, and actives that may be employed. For example, one may employ water-soluble hydrophilic polymers to help bind the actives to the site of application, moisturizers or humectants to help maintain moisture in the skin, sunscreen actives for absorbing and/or blocking UV light, colorants and cosmetic bases to mask over or cover the afflicted area of the skin. Typically, the compositions may, and preferably will, comprise a combination of such active components which further include, but are not limited to, moisturizers, colorants, light diffusers, softening agents, sunscreens, antioxidants, fragrances, vitamins, anti-inflammatory agents, moisturizers, tactile modifies, emollients, preservatives, chelators, thickeners, anti-inflammatory agents, penetrants, humectants, perilla oil or perilla seed, and the like as well as other botanicals such as aloe, chamomile, and the like, and mixtures of the foregoing. These and additional active agents, excipients and other additives are described briefly below as well as in the patents identified above with respect to the dermatologically acceptable carriers, especially Maniscalco—U.S. Pat. No. 7,078,022. Those skilled in the art will readily recognize and appreciate what additional ingredients may be employed in light of the intended performance of the formulated product and the delivery/application method to be used.

Suitable antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, tocopherols (e.g., tocopherol acetate), tocotrienols, curcurmin and its derivatives and ubiquinone. Natural extracts containing antioxidants suitable for use in the compositions of this invention, include, but are not limited to, extracts containing flavonoids and isoflavonoids and their derivatives (e.g., genistein and diadzein), extracts containing resveratrol and the like. Examples of such natural extracts include grape seed, green tea, pine bark, *Phyllanthus emblica* and propolis. Other examples of antioxidants may be found on pages 1612 13 of the ICI Handbook as well as in Ghosal—U.S. Pat. No. 6,124,268, both of which are incorporated herein by reference in their entirety.

The skin treatment compositions and cosmetic products of the present invention may also include one or more vitamins and/or their derivatives. Vitamins and vitamin derivatives include, for example, vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C and derivatives (for example ascorbyl palmitate, ascorbyl glucoside, and ascorbyl acetate), vitamin D, ergocalciferol (vitamin $D_2$), vitamin E, DL-α-tocopherol, tocopherol E acetate, tocopherol hydrogensuccinate, vitamin $K_1$, esculin (vitamin P active ingredient), thiamine (vitamin $B_1$), nicotinic acid (niacin), niacinamide, pyridoxine, pyridoxal, pyridoxamine, (vitamin $B_6$), pantothenic acid, biotin, folic acid and cobalamine (vitamin $B_{12}$). Preferred vitamins are, for example, vitamin A palmitate, vitamin C and derivatives thereof, DL-α-tocopherol, tocopherol acetate, nicotinic acid, pantothenic acid and biotin. Vitamin E, which is often added to cosmetic and personal care products is also preferably stabilized by a suitable stabilizer according to the invention.

Non-vitamin antioxidants are also suitable including, but are not limited to, BHT (butylated hydroxy toluene), L-ergothioneine (available as Thiotane™); tetrahydrocurcumin, carnosine, diethylhexyl syringylidene malonate (available as Oxynex® ST or Oxynex® ST Liquid from EMD Chemicals/Merck, Germany.), ubiquinone (co-enzyme Q10), Idebenone and combinations thereof.

Suitable emollients include those agents known for softening the skin which may be selected from hydrocarbons, fatty acids, fatty alcohols and esters. Petrolatum is a common hydrocarbon type of emollient conditioning agent. Other hydrocarbons that may be employed include alkyl benzoate, mineral oil, polyolefins such as polydecene, and paraffins, such as isohexadecane. Fatty acids and alcohols typically have from about 10 to 30 carbon atoms. Illustrative are myristic, isostearic, hydroxystearic, oleic, linoleic, ricinoleic, behenic and eruicic acids and alcohols. Oily ester emollients may be those selected from one or more of the following: triglyceride esters, acetoglyceride esters, ethoxylated glycerides, alkyl esters of fatty acids, ether esters, polyhydric alcohol esters and wax esters. Additional emollients or hydrophobic agents include $C_{12}$ to $C_{15}$ alkyl benzoate, dioctyladipate, octyl stearate, octyidodecanol, hexyl laurate, octyldodecyl neopentanoate, cyclomethicone, dicapryl ether, dimethicone, phenyl trimethicone, isopropyl myristate, capriylic/capric triglycerides, propylene glycol dicaprylate/dicaprate and decyl oleate, cyclomethicones and other silicone derivatives.

Suitable humectants include various polyhydric alcohols, especially polyalkylene glycols and, more preferably, alkylene polyols and their derivatives. Exemplary humectants include propylene glycol, dipropylene glycol, polypropylene glycol, polyethylene glycol, sorbitol, 2-pyrrolidone-5-carboxylate, hydroxypropyl sorbitol, hexylene glycol, ethoxydiglycol 1,3-butylene glycol, 1,2,6-hexanetriol, glycerin, ethoxylated glycerin, propoxylated glycerin, compatible solutes, such as ectoin, hydroxyectoin, taurines, carnitine, acetyl carnitine and mixtures thereof. When employed in effective amounts, generally from 1 to 30%, preferably from 2 to 20%, by weight of the compositions of the present invention, these additives serve as skin moisturizers as well as reduce scaling and stimulate the removal of built-up scale from the skin.

Although the meroterpenes have anti-inflammatory properties, the compositions of the present invention may further include one or more additional anti-inflammatory agents. Examples of anti-inflammatory ingredients include, but are not limited to, bisabolol, curcurmin and its derivatives, retinoids, flavonoids, terpenes and other polyphenolics etc. These and other anti-inflammatory agents are disclosed in Gupta et. al.—US 2005/0048008A1, which is incorporated herein by reference in its entirety. Compositions containing steroidal anti-inflammatory, non-steroidal anti-inflammatory, as well as "natural" anti-inflammatory, such as extract of the plant Aloe vera, are also included in the present invention and have been disclosed for such use. See e.g., U.S. Pat. No. 4,185,100, Rovee, (hydrocortisone, dexamethasone, naproxen, ketoprofen, ibuprofen); U.S. Pat. No. 4,338,293, Holick, (steroidal anti-inflammatories); Law, et al., Br. J. Pharmac., 59(4), 591-597 (1977) (ibuprofen); Kaidbey, J. Invest. Dermatoloy, 66, 153-156 (1976) (indomethacin); and Gruber, et al., Clinical Pharm. and Therapeut., 13(1), 109-113 (1971) (aspirin, fenoprofen).

Preferably, especially since the compositions of the present invention are intended to stay on the skin during the daylight hours, these compositions will contain one or more sunscreen actives. Sunscreen actives are of two types, inorganic actives that work by reflecting the UV light and organic actives that work, predominately, by absorbing UV energy. The amount of the sunscreen active to be incorporated into the sunscreen effective formulations is that which is conventional in the art. Typically, the amount is dependent upon, among other factors, the delivery means, e.g., is it applied as a spray or lotion; the stability of the active; the efficacy of the selected sunblock active itself; and the application rate, as well as the particular SPF desired. From the commercial perspective, another factor influencing the level of such sunscreen actives in the sunscreen effective formulations is the regulatory limitations on their use. In the United States, for example, strict controls are placed upon the maximum level at which approved sunscreen actives may be present. Regulatory controls may also dictate which sunscreen actives may be used in which countries.

Suitable organic sunscreen actives include, for example, butyl methoxydibenzoylmethane (avobenzone), benzophenone-8, dioxybenzone, homosalate, octylsalate, menthyl anthranilate, octocrylene, ethylhexyl methoxycinnamate (Octinoxate), oxybenzone, ethylhexyl salicylate (Octisalate), benzophenone-3, ethylhexyl dimethyl PABA (Padimate O), glyceryl PABA, phenylbenzimidazole sulfonic acid, sulfisobezone, trolamine salicylate, 4-methylbenzylidene camphor, bisoctriazole, bemotrizinol, ecamsule, drometrizole trisiloxane, disodium phenyl dibenzimidazole tetrasulfonate, diethylamine hydroxybenzoyl hexyl bezoate, octyl triazone, hexyl benzoate, benzophenone-4, ethyhexyl triazone, diethylhexyl butamido triazone, bisimidazylate, polysilicone-15, etc.

Inorganic sunscreens include, but are not limited to, microfine surface treated titanium dioxide and microfine untreated and surface treated zinc oxide. The titanium dioxide in the sunscreen compositions preferably has a mean primary particle size of between 5 and 150 nm, preferably between 10 and 100 nm. Titanium oxide may have an anatase, rutile, or amorphous structure. The zinc oxide in the sunscreen compositions preferably has a mean primary particle size of between 5 nm and 150 nm, preferably between 10 nm and 100 nm. Examples of suitable hydrophobically modified titanium dioxide compositions include but are not limited to: UV Titans® X161, M160, M262 (surface treated with stearic acid and alumina) (Kemira); Eusolex® T-2000 (surface treated with alumina and simethicone) (Merck KGaA); T-Cote® (surface treated with dimethicone) (BASF); Mirasun® TiW60 (surface treated with silica and alumina) (Rhodia); Tayaca MT100T (surface treated with aluminum stearate) (Tayaca); Tayaca MT-100SA (surface treated with silica and alumina) (Tayaca); Tayaca MT-500SA (surface treated with silica and alumina) (Tayaca); Tioveile EUT, FIN, FLO, FPT, GCM, GPT, IPM, MOTG, OP, TG, TGOP (surface treated with silica and alumina, 40% dispersion in a range of cosmetic vehicle) (ICI); Eusolexe T-45D (surface treated with alumina and simethicone, 45% dispersion in isononoyinonaoate) (Merck KGaA); and Eusolex® T-Aqua (surface treated with aluminum hydroxide, 25% dispersion in water) (Merck KGaA). Examples of suitable untreated and hydrophobically modified zinc oxide include but are not limited to: Z-Cote® (uncoated microfine zinc oxide) (BASF); Z-Cote® HP-1 (surface treated with dimethicone) (BASF); Sachtotec® LA 10 (surface treated with lauric acid) (Sachtleben); Sachtotec® (uncoated microfine zinc oxide) (Sachtleben); Spectraveil® FIN, IPM, MOTG, OP, TG, TGOP (uncoated, 60% dispersion in a range of cosmetic vehicle) (ICI); Z-sperse® TN (untreated, dispersion in C12-15 alkyl benzoate) (Collaborative); Z-sperse® TN (untreated, dispersion in octydodecyl neopentanoate) (Collaborative).

Most preferably, a combination of such sunscreen actives will be employed. In this respect, it is well known that certain sunscreen actives have better stability, hence longevity, than others; while others have better absorptive capabilities, whether in reference to selectivity for UV energy of certain wavelength(s) or cumulative absorptive capabilities. Suitable combinations of sunscreen actives are well known in the art and within the skill of a typical artisan in the field.

If needed, suitable photostabilizers, for example, diethylhexyl benzylidene malonates (Oxynex® ST or Oxynex® ST Liquid marketed by EMD/Merck, Germany), 4-methylbenzylidene camphor, butyloctyl salicylate, diethylhexyl 2,6- naphthalate (Corapan® TQ, marketed by Symrise) etc. can also be included to stabilize unstable sunscreen actives. Additionally, synergistic agents may be used in combination with one or more sunscreen compositions including, for example, bakuchiol. Such synergistic combinations are disclosed in our co-pending, parent U.S. patent application Ser. No. 11/803,188 entitled "Sunscreen Compositions and Methods" and filed on May 14, 2007, which is incorporated herein by reference in its entirety.

The skin care compositions of the present invention may be used to effect various objectives. For example, they may be formulated to maintain or at least retard the effect of aging and other factors on the overall appearance and/or tone of one's skin. Similarly, they may be formulated to effectuate an improvement in the overall appearance and/or tone of one's skin where the adverse consequences of skin aging and other factors have already begun to manifest themselves. Finally, they can be formulated to address specific skin conditions on specific areas of the body, most notably to address, for example, lines and creases on the forehead, crow's feet, sagging under the eyes, etc. The latter may be accomplished by, for example, formulating compositions with higher concentrations of the meroterpene and applying that composition directly to the afflicted area.

Generally, in topical and intradermal use, the appropriate formulation is applied to the surface of or injected into the skin to be treated. The amount of the topical or intradermal composition to be applied to the skin will again depend upon the specific composition or product and its objective. In the case of topical compositions having an additional functionality, especially where the meroterpene is added to a conventional skin care product, each composition or product will be applied in an amount and manner traditionally employed for such comparable conventional products that are free of the meroterpenes. For most applications, though, the quantity of the inventive compositions and products to be applied per application are, in mg composition/$cm^2$ skin, from about 0.1 mg/$cm^2$ to about 10 mg/$cm^2$. A particularly useful application amount is from about 1 mg/$cm^2$ to about 2 mg/$cm^2$.

The frequency and period of application for the skin treatment compositions and cosmetic products of the present invention will also vary widely depending upon the nature of the composition or product, including its form, concentration, intended function, etc. In essence, each is applied in an amount and for a sufficient period of time and with such frequency as is necessary to achieve the gene manipulation objective of the meroterpene component. For example, in the case of fine lines, wrinkles and the like, the composition would typically be applied once, twice, or more daily in an amount sufficient to wet or cover the afflicted skin and left in place. These compositions would typically be re-applied for one week, two weeks, four weeks, or more as necessary until the disorder is no longer present, or is improved to the satisfaction of the individual. Thereafter, a daily or a more or less frequent application could be continued for a month, several months or more for prophylactic or preventative purposes. Additionally, the frequency and duration of application may be adjusted depending upon the severity of the condition being addressed and the concentration of the meroterpene.

Compositions intended to prevent or delay the onset of aging and other environmental and physiological factors on skin in an effort to maintain a more youthful skin tone and appearance are to be applied to the skin on a chronic basis. In particular, the composition will be applied to those areas of the skin that are more susceptible to skin aging and other factors, especially the face, neck and upper surface of the hands. Alternatively, especially for an overall benefit, the composition is applied to all or large portions of the skin on a daily or other basis and to the aforementioned more susceptible areas on a more frequent basis. While a maximum benefit or noticeable change in skin appearance may be achieved after several weeks, months, or years of use, one may continue to apply the cosmetic product daily or less frequently, perhaps once or twice a week, once a satisfactory result is attained, in order to maintain that skin condition or at least delay or lessen the impact of aging. These products are typically of the type that are intended to be "left on" once applied. In this respect, these compositions are especially useful as overnight treatments.

As noted above, the skin treatment compositions and cosmetic products according to the present invention can be applied to any skin surface for its intended function. While most commonly applied to the external surface of the face and/or certain facial features including face, lips, under eye area, eyelids, eyebrows, ears, and cheeks, they are equally applicable to the scalp, neck, shoulders, arms, torso, feet, hands, fingers, toes, etc. The compositions and products according to the present invention are preferably applied in the form of a lotion, cream, gel, foam, ointment, paste, wax-stick, emulsion, dispersion, liposome, coacervate, spray, conditioner, tonic, cosmetic (including foundation, base and other make-up), lipstick, after-shave, skin cleanser, moisturizer, or the like. Alternatively, the compositions and products according to the present invention may be in the form of a substrate-based product wherein the inventive composition is impregnated into or onto a substrate, most typically a woven and/or non-woven wipe, pad, patch, tissue, mask, and the like.

Delivery Methods for the Compositions

The compositions and products according to the present invention may be delivered directly from the package or container to the skin to be treated, transferred to the users hand or fingers for application, or to another substrate for application including, for example, pads, cotton balls, wipes, masks, applicators and the like. In the case of direct application, the composition may be squeezed from a tube or sprayed from a spray container. Alternatively, there are a number of applicator devices that carry or store the composition and are configured to deliver them as well. For example, the compositions can be incorporated into and delivered from a soft-tipped or flexible dispensing device. These devices are useful for the controlled delivery of the compositions to the skin surface and have the advantage that the treatment composition itself never need be directly handled by the user. Non-limiting examples of these devices comprise a fluid container including a mouth, an applicator, means for holding the applicator in the mouth of the container, and a normally closed pressure-responsive valve for permitting the flow of fluid from the container to the applicator upon the application of pressure to the valve. The valve can include a diaphragm formed from an elastically fluid impermeable material with a plurality of non-intersecting accurate slits therein, where each slit has a base which is intersected by at least one other slit, and where each slit is out of intersecting relation with its own base, and wherein there is a means for disposing the valve in the container inside of the applicator. Examples of these applicator devices are described in U.S. Pat. No. 4,693,623 (Schwartzman), U.S. Pat. No. 4,620,648 (Schwartzman), U.S. Pat. No. 3,669,323 (Harker et al.), U.S. Pat. No. 3,418,055 (Schwartzman), and U.S. Pat. No. 3,410,645 (Schwartzman), all of which are incorporated herein by reference in their entirety.

As noted above, the inventive compositions can be impregnated into a substrate-based delivery means. For example, in order to ensure a continuous exposure of the skin to at least a minimum level of the dermatological acid and meroterpene, the composition may be impregnated into a patch that is then applied to the skin. Such an approach is particularly useful for those affected skin areas and other skin disorders needing more intensive treatment. The patch can be occlusive, semi-occlusive or non-occlusive and can be adhesive or non-adhesive. The compositions of the present invention comprising the meroterpene(s) and, if present, the additional skin care active(s) can be contained within the patch or be applied to the skin prior to application of the patch. The patch is preferably left on the skin for a period of at least about 5 minutes to as long as 1 hour or more, preferably at night as a form of night therapy. Examples of such devices are disclosed in U.S. Pat. Nos. 5,146,846; 5,223,262; 4,820,724; 4,379,454; and 4,956,171, all of which are hereby incorporated herein by reference.

Another substrate-based delivery means is the cleansing pad. Preferably these pads comprise from about 50% to about 75% by weight of one or more layers of non-woven fabric material and from about 20% to about 75% by weight (on dry solids basis) of a water soluble polymeric resin. Examples of pads are described in U.S. Pat. No. 4,891,228; (Thaman et al.) and U.S. Pat. No. 4,891,227 (Thaman et al.), both of which are incorporated by reference herein in their entirety.

Continual, preferably daily, use of the skin treatment compositions of the present invention, regardless of whether one anticipates UV exposure or not, provide a number of additional benefits to ones skin. For example, the continual use of these skin treatment compositions will delay the appearance of fine lines, enhance extra-cellular matrix cohesion, reduce the appearance of spider veins, improving skin firmness and elasticity: skin effects that are not only a result of exposure to the sun but also the natural aging process. In essence, the long-term benefits of the continual use of the skin treatment compositions of the present invention include the lessening or delayed manifestation, possibly even the prevention or repair, of skin damage and will manifest itself in an overall improved skin quality as compared to skin on which a meroterpene-free skin treatment composition had been applied on an on-going basis. For example, the long-term use of the inventive skin treatment compositions may help with thickening the keratinous tissue (i.e., building and improving the strength and elasticity of the epidermis and/or dermis layers of the skin, increasing cell mitosis, and heightening and improving the overall performance of the dermal-epidermal junction), thereby preventing and/or retarding atrophy of human skin; preventing and/or retarding the appearance of spider veins and/or red blotchiness on human skin; preventing and/or retarding the appearance of dark circles under the eye; preventing and/or retarding shallowness and/or sagging of human skin; soften and/or smooth lips; preventing and/or relieving itch of human skin, regulating skin texture (e.g. wrinkles and fine lines), improving skin color (e.g. redness, freckles); and the like.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

In the foregoing and in the following examples, all temperatures are set forth uncorrected in degrees Celsius; and, unless otherwise indicated, all parts and percentages are by weight.

Example 1

Gene Regulation with Bakuchiol

A comparative DNA microarray high-throughput screening of bakuchiol and retinol was conducted to ascertain the suitability of employing meroterpenes, most notably bakuchiol, as a substitute for retinol in addressing various skin conditions. Surprisingly, bakuchiol, whose structure is completely dissimilar to those of retinoids, has been found to have a retinol-like gene expression profile. Indeed, in many respects, the bakuchiol provided an improved, marked up-regulation of certain genes beneficially associated with skin and skin conditioning as compared to retinol, a well known and commercially employed active for improving skin conditions. Additionally, bakuchiol was found to down regulate or have a lesser up-regulation of other genes which have an adverse effect or enhance the consequences of aging on skin. In contrast, certain of these genes were up-regulated or experienced a higher degree of up-regulation with retinol, respectively. Consequently, it was found that meroterpenes, especially bakuchiol, provided an ideal, if not superior, replacement for the near utopian retinoids in skin care products and treatments.

In the present study, a gene assay was conducted using EpiDerm tissues obtained from Mattek (Ashland, Mass.) and cultured according to the manufacturer's instructions. The test materials—retinol (50% active) and bakuchiol (Trade named, Sytenol A, 95.5% purity) were dissolved in DMSO at 10 mg/ml (retinol) and 5 mg/ml (Sytenol A), and further dilutions were made in type I sterile water. Test materials were assayed at 10 µg/ml (retinol) and 5 µg/ml (Sytenol A) against 0.1% DMSO control. The incubation time with skin tissues was 2 days. After incubation, skin tissues were harvested, frozen in liquid nitrogen, and subjected to RNA extraction with a Qiagen kit. The quality of the extracted RNA was validated twice by electrophoresis (after extraction and before microarray analysis).

The test samples were hybridized and data were analyzed using human OneArray platform from Phalanx Biotech (Palo Alto, Calif.; for more information about this platform see www.phalanxbiotech.com/Power/Power.html). The resultant file yielded information on over 30,000 probes and was then culled to select the dermatologically relevant genes and to eliminate those results manifesting a high (greater than 0.05) predictor values and a low (less than 1.5) fold change as compared to the DMSO control. The term, "p-value" is used herein to mean the probability that the results were not significant: for example, a p-value of 0.05 means that there are 5 chances in 100 that the results are not significant. The term "fold change" refers to the extent, as compared to the DMSO control, that the active produced an increase or decrease in gene and corresponding protein expression. A 1.5 fold increase means that 1.5 times as much of the corresponding protein was produced in those cells exposed to the active as compared to those only exposed to the DMSO control.

"Modulating" or "regulating" a gene refers to the ability of a compound to affect the ability of that gene to induce the production of the corresponding protein which is then capable of performing at least one of its biological activities to at least some extent. According to the present invention, results were only considered if there was at least a 1.5-fold, preferably at least a 2-fold, change in gene expression. Up-regulation (presented as a positive fold change) is a process which occurs within a cell triggered by a signal (originating internal or external to the cell) which results in an increased expression of one or more genes and as a result the protein(s)

encoded by those genes. Conversely down-regulation (presented as a negative fold change) is a process resulting in decreased gene and corresponding protein expression. Up-regulation occurs for example when a cell is deficient in some kind of receptor. In this case, more receptor protein is synthesized and transported to the membrane of the cell and thus the sensitivity of the cell is brought back to normal, reestablishing homeostasis. Down-regulation occurs for example when a cell is overly stimulated by a neurotransmitter, hormone, or drug for a prolonged period of time and the expression of the receptor protein is decreased in order to protect the cell. This homeostasis can be achieved by using external agent with beneficial effects to skin.

The results attained on the effects of retinol and Sytenol A bakuchiol on dermatologically relevant gene expressions are summarized and presented in the following sections and tables.

Retinoic Acid Receptor Genes

The retinoic acid receptor (RAR) is a type of nuclear receptor which is activated by both all-trans retinoic acid and 9-cis-retinoic acid. There are three retinoic acid receptors: RAR-alpha, RAR-beta, and RAR-gamma. RAR-gamma has been ascribed to be the cause of skin irritation. The retinoic acid receptors regulate specific subsets of target genes during all-trans retinoic acid (RA) induced cell differentiation. Retinol binding proteins are carrier proteins which bind retinol. The gene encoding cellular retinol (ROL)-binding protein type I (RBP1) is indispensable for efficient RA synthesis and storage [Norbert B. Ghyselinck et al, *The EMBO Journal* (1999) 18, 4903-4914]. Cellular retinoic acid-binding protein 1 (CRABP-1) is assumed to play an important role in retinoic acid-mediated differentiation and proliferation processes. CRABP1 is structurally similar to the cellular retinol-binding proteins, but binds only retinoic acid. Interestingly, Sytenol A bakuchiol has very specific receptor specificity over retinol and has no effect on the RAR-beta and RAR-gamma receptors and down-regulates CRABP-1. A complete lack of RAR-gamma receptor specificity demonstrates that Sytenol A has no skin irritation effect.

TABLE 1

Retinoic Acid Receptor gene expression by retinol and Sytenol A

| | | Fold Change | |
|---|---|---|---|
| Gene | Gene Description | Retinol | Sytenol A |
| RARB | Retinoic acid receptor beta-1 | +5.63 | No effect |
| RARRES1 | Retinoic acid receptor responder protein 1 | +13.25 | +12.87 |
| RBP1 | Cellular Retinol-binding protein-I | +2.6 | +4.17 |
| RBP2 | Cellular Retinol-binding protein-II | No effect | +4.12 |
| RARG | Retinoic acid receptor gama-1 | +1.87 | No effect |
| CRABP1 | Cellular retinoic acid-binding protein 1 | +2.83 | −2.91 |
| RBP7 | Cellular retinoic acid-binding protein 4 | No effect | +3.09 |

Retinol Metabolism Genes

Synthesis of retinoic acid from retinol is a two-step process in which alcohol dehydrogenases perform the oxidation of vitamin A to all-trans-retinaldehyde, followed by oxidation of the latter to all-trans-retinoic acid by retinaldehyde dehydrogenases, which is the rate-limiting step in its production. Esterification of retinol with long-chain fatty acids by lecithin-retinol acyltransferase is an important step in both the absorption and storage of retinol. Cutaneous cytochromes P450 enzymes (CYP gene products) involved in oxidative metabolism and disposition of endogenous and foreign compounds, including environmental toxins, natural products, and drugs (Liping Du, Mark M. Neis, Patricia A. Ladd, and Diane S. Keeney, Journal of Pharmacology And Experimental Therapeutics Fast Forward First published on Sep. 19, 2006; DOI: 10.1124/jpet.106.111724). Cytochromes P450 1A1 and P450 1A2 are present in human skin and are involved in the oxidation of all-trans & 9-cis retinol to retinoic acid and in catabolism of retinoic acid to 4-hydroxy retinoic acid. Retinol and Sytenol A have very similar retinol metabolism gene expression profiles except that Lecithin retinol acyltransferase is up-regulated by Sytenol A almost seven-fold higher than by retinol. This up-regulation helps in the improvement of absorption and storage of endogenous retinol.

TABLE 2

Retinol metabolism gene expression profile of retinol and Sytenol A

| | | Fold Change | |
|---|---|---|---|
| Gene | Gene Description | Retinol | Sytenol A |
| LRAT | Lecithin retinol acyltransferase | +12.3 | +82.23 |
| NT5C1B, RDH14 | Retinol dehydrogenase 14 (Alcohol dehydrogenase PAN20 | −5.33 | −3.57 |
| RETSAT | All-trans-retinol 13,14-reductase precursor | −2.97 | −2.84 |
| DHRS9 | NADP-dependent retinol dehydrogenase/reductase | +5.48 | +11.56 |
| CYP26B1 | Cytochrome P450 26B1 (Retinoic acid-metabolizing cytochrome) | +1.87 | −1.74 |
| CYP1A1 | Cytochrome P450 1A1 | +4.04 | +4.88 |
| CYP1A2 | Cytochrome P450 1A2 | +3.62 | +6.65 |

Extracelluar Matrix Proteins

The extracellular matrix (ECM) provides a scaffolding and structural support for cells and organs. Additionally, it is capable of exchanging information with cells and thereby modulates a whole host of processes including development, cell migration, attachment, differentiation, and repair. The ECM consists of the following quintet: basement membrane (BM), collagen, elastin, proteoglycans (glycosaminoglycans—GAGs) and hyaluronan, and cell adhesion molecules (CAMs).

Dermal-Epidermal Proteins

Laminins are the most abundant structural non-collagenous glycoproteins ubiquitously present in basement membranes. Laminins display a remarkable repertoire of functions, most importantly as structural elements forming a network throughout the basement membrane to which other collagenous or non-collagenous glycoproteins and proteoglycans attach. Laminins critically contribute to cell attachment and differentiation, cell shape and movement, maintenance of tissue phenotype, and promotion of tissue survival. Furthermore, they are signaling molecules providing adjacent cells with diverse information by interacting with cell surface components. Both retinol and Sytenol A up-regulate Laminins: however, Sytenol A up-regulates almost three-fold more than retinol.

The integrins are a newly defined family of cell surface receptors. Integrins belong to particles that are very important for maintaining the dermal-epidermal junction as well as cell-to-cell connections. They are involved in the adhesion of cells to the extracellular matrix and to other cells. Integrins and their ligands may be required for complex physiological and pathophysiological events, such as epidermal differentiation, inflammation, immune response, wound healing or tumor progression [Berman A E, Kozlova N I, Morozevich G E. Integrins: structure and signaling. Biochemistry (Moscow). 68(12):1284-1299, 2003, Xiong J-P, Stehle T, Goodman S L, Arnaout M A. New insights into the structural basis of integrin activation. Blood.; 102(4):1155-1159, 2003]. Some of the integrin receptor molecules are expressed in a distinct distribution pattern within the skin. Three of them are found selectively in the basal layer of the epidermis: suggesting an important role in the establishment of the functional integrity of the dermal-epidermal junction. Interestingly, like retinal, Sytenol A up-regulated Integrin beta 4 and 6 precursors which is similar to retinal; yet, Sytenol A has practically no effect on Integrins alpha-7-precursor, Integrin beta-5-precursor and Integrin beta-like 1, whereas retinol has a significant down-regulatory effect. Accordingly, it is expected that Sytenol A will provide better improvement over retinol in maintaining the dermal-epidermal junction as well as cell-to-cell connections.

Collagen IV is the major constituent of the Lamina densa of the dermal-epidermal junction whose optimum physiological state depends upon there being a sufficient amount of collagen IV. Another key protein present in the lamina densa is heparin sulfate proteoglycan (perlecan). Collagen XVII is a transmembrane constituent of the dermal-epidermal junction anchoring complex. Therefore, in order to maintain or restore the optimal physiological state of the dermal-epidermal junction, it is desirable to have a means of increasing the amount of collagen IV, collagen XVII and heparin sulfate. It has now been found that collagen IV chain precursor and collagen XVII chain precursor are significantly up-regulated by Sytenol A as compared to retinol. Likewise, significant up-regulation of heparin sulfate 3-O-sulfotransferase 1 precursor (which is essential to the formation of heparin sulfate) was also observed with Sytenol A. Consequently, it is expected that Sytenol A will provide better maintenance of integrity and function of basement membrane of the DEJ over retinol.

Nidogens are considered classical linkers joining laminin and collagen IV in the basement membrane. Unlike retinol which manifested a significant down-regulation in nidogens, Sytenol A appeared to have essentially no effect on nidogens. Accordingly, Sytenol A is not likely have an adverse affect on the existing structure; thus, in this regard, maintaining the existing properties of the dermal-epidermal junction.

TABLE 3

Dermal-epidermal gene expression profile of retinol and Sytenol A

| Gene | Gene Description | Fold Change Retinol | Sytenol A |
|------|------------------|---------|-----------|
| LAMA3 | Laminin subunit alpha-3 precursor (Epiligrin 170 kDa subunit) | +4.70 | +11.03 |
| LAMC2 | Laminin subunit gamma-2 precursor (Laminin B2t chain) | +2.68 | +7.84 |
| ITGA6 | Integrin alpha-6 precursor | No effect | +3.57 |
| ITGA7 | Integrin alpha-7 precursor | −5.53 | No effect |
| ITGB2 | Integrin beta-2-precursor | −3.54 | −7.67 |
| ITGB4 | Integrin beta-4-precursor | +3.48 | +7.97 |
| ITGB5 | Integrin beta-5 precursor | −2.42 | No effect |
| ITGB6 | Integrin beta-6-precursor | +7.49 | +7.71 |
| ITGB8 | Integrin beta-8 precursor | No effect | +3.90 |
| COL4A6 | Collagen alpha-6 (IV) chain precursor | +6.41 | +11.20 |
| COL17A1 | Collagen alpha-1 (XVII) chain precursor | +3.5 | +8.7 |
| HS3ST1 | Heparan sulfate glucosamine 3-O-sulfotransferase 1 precursor (Heparan sulfate 3-O-sulfotransferase 1) | +8.65 | +24.91 |
| NID2 | Nidogen-2-precursor | −17.36 | No effect |

Collagen

Collagen is the main protein of connective tissue and the most abundant protein in mammals, making up about 25% of the whole-body protein content. Collagen has great tensile strength, and is the main component of fascia, cartilage, ligaments, tendons, bone and teeth. Tough bundles of collagen called collagen fibers are a major component of the extracellular matrix that supports most tissues and gives cells structure. While typically extracellular, collagen is also found inside certain cells. Along with soft keratin, collagen is responsible for skin strength and elasticity, and its degradation leads to wrinkles that accompany aging.

Collagen I is the most abundant collagen of the human body. It is present in scar tissue, the end product when tissue heals by repair. It is found in tendons, skin and artery walls. As noted above, skin aging occurs through two biologically distinct processes: intrinsic and extrinsic aging. The first is a naturally occurring process that results from slow tissue degeneration. In human dermis, intrinsic aging is characterized by three features: atrophy of the dermis due to loss of collagen, degeneration in the elastic fiber network, and loss of hydration. In contrast, extrinsic aging is due to environmental factors, especially ultraviolet (UV) light exposure: the latter often referred to as photoaging. At the microscopic level, the distinguishing feature of photoaging is a massive accumulation of elastotic material in the upper and middle dermis, a process termed solar elastosis (Uitto J, The role of elastin and collagen in cutaneous aging: intrinsic aging versus photoexposure, J Drugs Dermatol, 7(2 Suppl):s12-16, 2008).

Proteins of the matrix metalloproteinase (MMP) family are involved in the breakdown of extracellular matrix in normal physiological processes, such as embryonic development, reproduction, and tissue remodeling, as well as in disease processes, such as arthritis and metastasis. Most MMP's are secreted as inactive proproteins which are activated when cleaved by extracellular proteinases. MMPs are also thought to play a major role on various cell behaviors such as cell proliferation, migration (adhesion/dispersion), differentiation, angiogenesis, apoptosis and host defense.

The precursor of matrix metalloproteinase 9 (pro-MMP-9) forms a complex with the tissue inhibitor of metalloproteinases (TIMP)-1 through the C-terminal domain of each molecule, and the N-terminal domain of TIMP-1 in the complex interacts and inhibits active MMPs. Fibroblasts almost completely shut down collagen I gene transcription in the presence of increased collagen triple helix repeat-containing protein 1 (CTHRC1). CTHRC1 over-expression caused a dramatic reduction in collagen type I mRNA and protein levels (Pyagay P, Heroult M, Wang Q, Lehnert W, Belden J, Liaw L, Friesel R E, Lindner V, Collagen triple helix repeat containing 1, a novel secreted protein in injured and diseased arteries, inhibits collagen expression and promotes cell migration, Cir Res, 96(2):261-268, 2005).

MMP-26 is important in connective tissue remodeling and pathobiology of various benign skin disorders. The expression pattern of MMP-26 suggests that it may be up-regulated in basal keratinocytes even without tumorogenesis because of altered cell-matrix interactions and inflammation and, unlike most MMPs, becomes down-regulated during histological dedifferentiation of Squamous cell cancers (SCC). Thus, a lack of MMP-26 in SCC could be a marker of aggressive growth (Ahokas K, Skoog T, Suomela S, Jeskanen L, Impola U, Isaka K and Saarialho-Kere U, Matrilysis-2 (Matrix Metalloprotease-26) is up-regulated in keratinocytes during wound repair and early skin carcinogenesis, J Invest Dermatol, 124:849-856, 2005)

MMP-28 is needed to restructure the basement membrane and to degrade adhesive proteins between keratinocytes to supply new cells for the migrating front (Saarialho-Kere U, Kerkela E, Jahkola T, Suomela S, Keksi-Oja J, Lohi J, Epilysin (MMP-28) expression is associated with cell proliferation during epithelial repair, J Invest dermatol, 119(1):14-21, 2002).

Fibronectin

Fibronectin is a high-molecular-weight extracellular matrix glycoprotein containing about 5% carbohydrate that binds to membrane spanning receptor proteins called integrins. In addition to integrins, they also bind extracellular matrix components such as collagen, fibrin and heparan sulfate.

Fibronectin has numerous functions that ensure the normal functioning of life. One of its more notable functions is its role as a 'guide' in cellular migration pathways in mammalian development, particularly the Neutral crest (ectoderm cells that will develop into skin pigment cells as well as some bones of the skull). Fibronectin helps maintain the shape of cells by lining up and organizing intracellular cytoskeleton by means of receptors. It helps stabilize the attachment of extracellular matrix (ECM) to cells by acting as binding sites for cell surface receptors. More generally though, fibronectin helps create a cross-linked network within the extracellular matrix by having binding sites for other ECM components.

TABLE 4

Extracellular Matrix proteins and proteases

| | | Fold Change | |
|---|---|---|---|
| Gene | Gene Description | Retinol | Sytenol A |
| COL1A2 | Collagen alpha-2 (I) chain precursor (Alpa-2 type I collagen) | +3.31 | +1.85 |
| COL3A1 | Collagen alpha-1 (III) chain precursor | −2.36 | No effect |
| COL9A2 | Collagen alpha-2 (IX) chain precursor | +5.56 | +6.67 |
| COL9A3 | Collagen alpha-3 (IX) chain precursor | +4.05 | +5.76 |
| CTHRC1 | Collagen triple helix repeat-containing protein 1 precursor | −18.94 | −10.17 |
| FNDC7 | Fibronectin type III domain containing 7 | No effect | +9.14 |
| FLRT2 | Fibronectin-like-domain-containing leucine-rich transmembrane protein 2 | −2.67 | No effect |
| FLRT3 | Fibronectin-like-domain-containing leucine-rich transmembrane protein 3 | +2.77 | +6.18 |
| MMP9 | Matrix metalloprotease-9-precursor | +8.35 | +12.61 |
| MMP15 | Matrix metalloprotease-15 precursor | +3.67 | +4.19 |
| MMP21 | Matrix metalloprotease-21 precursor | No effect | −7.89 |
| MMP23A, MMP23B | Matrix metalloprotease-23 | −5.78 | −8.83 |
| MMP28 | Matrix metalloprotease-28-precursor | +3.88 | +15.91 |
| MMP26 | Matrix metalloprotease-26-precursor (MMP-26) | +4.31 | +2.91 |
| ECM1 | Extracellular matrix protein 1 precursor | No effect | +2.00 |
| ECM2 | Extracellular matrix protein 2 precursor | +4.98 | +4.10 |
| SRRM1 | Serine/arginine repetitive matrix protein 1 (SR-related nuclear matrix protein 160 kDa) (SRm160) | +3.57 | +3.13 |

Elastin

Elastin is a protein in connective tissue that is elastic and allows many tissues in the body to resume their shape after stretching or contracting. Elastase breaks down elastin, an elastic fiber that, together with collagen, determines the mechanical properties of connective tissue. Elastase has been shown to disrupt tight junctions, cause proteolytic damage to tissue, break down cytokines and alpha proteinase inhibitor, cleave immunoglobulin A and G (IgA, IgG), and cleave both C3bi, a component of the complement system. OK In clinical studies, the formation of facial wrinkles has been closely linked to the loss of elastic properties of the skin. Cumulative irradiation with ultraviolet (UV) B at suberythemal doses significantly reduces the elastic properties of the skin, resulting in the formation of wrinkles. In in-vitro studies, a paracrine pathway has been identified between keratinocytes and fibroblasts, which leads to wrinkle formation via the up-regulation of fibroblast elastases that degrade elastic fibers (Imokawa G, Recent advances in characterizing biological mechanisms underlying UV-induced wrinkles: a pivotal role of fibroblasts-derived elastase, Arch Dermatol Res, 300 Suppl 1:S7-20, 2008). Based on the gene assay, Sytenol A is expected to maintain the desired level of Elastin required for maintaining the connective tissue structure due to its up-regulation of elastase inhibitors.

TABLE 5

Gene expression profile of Elastin

| | | Fold Change | |
|---|---|---|---|
| Gene | Gene Description | Retinol | Sytenol A |
| PI3 | Elastase-specific inhibitor | +2.45 | +2.72 |
| SERPINB1 | Leukocyte elastase inhibitor | +3.80 | +6.09 |
| ELA3B | Elastase-3B precursor (Elastase IIIB) | +5.89 | +6.58 |

Proteoglycans & Heparan Sulfate

Proteoglycans represent a special class of glycoproteins that are heavily glycosylated. They consist of a core protein with one or more covalently attached glycosamineglycan (GAG) chain(s). Proteoglycans are a major component of the extracellular matrix, the "filler" substance existing between cells in an organism. Here they form large complexes, both to other proteoglycans, to hyaluronana and to fibrous matrix proteins (such as collagen). They are also involved in binding cations (such as sodium, potassium, and calcium) and water, and also regulating the movement of molecules through the extracellular matrix. Evidence also shows they can affect the activity and stability of proteins and signaling molecules within the extracellular matrix. Hyaluronan is responsible for the water content of skin, where half the hyaluronan of the body is present. Age related changes in proteoglycan distribution exist and correlate with morphologic and functional changes that occur in the intrinsic process of aging in human skin (Willen M D, Sorrell J M, Lekan C C, Davis B R and Caplan A I, Patterns of glycosaminoglycan/proteogkycan immunostaining in human skin during aging, J Invest Dermatol, 96(6):968-974, 1991).

Essential to the formation of Hyaluronan synthase is a range of biosynthetic enzymes, such as sulfotransferase. The sulfuryl transfer reaction plays a key role in various biological processes such as cell communication, growth and development, and defense. Favorable proteoglycan gene modulation was observed with Sytenol A as compared to that effected by retinol.

TABLE 6

Gene expression profile of Proteoglycan and Heparan sulfate

| | | Fold Change | |
|---|---|---|---|
| Gene | Gene Description | Retinol | Sytenol A |
| HS6ST1 | Heparan sulfate 6-O-sulfotransferase 1 | +2.26 | +1.79 |
| HS3ST1 | Heparan sulfate 3-O-sulfotransferase 1 | +8.65 | +24.91 |
| NDST4 | N-heparan sulfate sulfotransferase 4 | No effect | +4.43 |
| HAS2 | Hyaluronan synthase 2 | −3.48 | No effect |
| HAS3 | Hyaluronan synthase 3 | +10.88 | +19.29 |
| HYAL1 | Hyaluronidase-1-precursor | +2.16 | No effect |

Cell Adhesion Molecules

Cell Adhesion Molecules (CAMs) are proteins located on the cell surface and are involved with binding those cells with other cells or with the extracellular matrix (ECM) in a process called cell adhesion. These proteins are typically transmembrane receptors and are composed of three domains: an intracellular domain that interacts with the cytoskeleton, a transmembrane domain and an extracellular domain that interacts either with other CAMs of the same kind (homophilic binding) or with other, dissimilar CAMs or the extracellular matrix (heterophilic binding).

The CAMs belong to 4 protein families: Ig (immunoglobulin) superfamily (IgSF CAMS), the integrins, the cadherins, and the selectins. The immunoglobulin superfamily (IgSF) is a large group of cell surface and soluble proteins that are involved in the recognition, binding, or adhesion processes of cells.

Integrins are cell surface receptors that interact with the extracellular matrix (ECM) and mediate various intracelluar signals. They define cellular shape, mobility, and regulate the cell cycle. These integral membrane proteins are attached to the cellular plasma membrane through a single transmembrane helix. Integrin plays a role in the attachment of cells to other cells, and also plays a role in the attachment of a cell to the material part of a tissue that is not part of any cell (the extracellular matrix). Besides the attachment role, integrin also plays a role in signal transduction, a process by which a cell transforms one kind of signal or stimulus into another. Two main functions of integrins are: (a) attachment of the cell to the ECM and (b) signal transduction from the ECM to the cell.

Cadherins are a class of type-1 transmembrane proteins. They play important roles in cell adhesion, ensuring that cells within tissues are bound together. They are dependent on calcium ($Ca^{2+}$) ions to function, hence their name. The cadherin superfamily includes cadherins, protocadherins, desmogleins, and desmocollins, and more. In structure, they share cadherin repeats, which are the extracellular $Ca^{2+}$-binding domains. There are multiple classes of cadherin molecule, each designated with a one-letter prefix (generally noting the type of tissue with which it is associated). Cadherins within one class will bind only to themselves. For example, an E-cadherin will bind only to another E-cadherin molecule. Manipulation of E-cadherin function may provide a means of altering epithelial integrity and, if enhanced, could provide greater resistance to infection with adenovirus and possibly other pathogens.

The selectins are a family of heterophilic CAMs that bind fucosylated carbohydrates, e.g. mucins. They are calcium-dependent. The three family members are E-selectin (endothelial), L-selectin (leukocyte)) and P-selectin (platelet).

Sytenol A has shown favorable modulatory effects on cell adhesion genes thereby providing improved cell adhesion.

TABLE 7

Gene expression profile of cell adhesion molecules

| | | Fold Change | |
|---|---|---|---|
| Gene | Gene Description | Retinol | Sytenol A |
| | Immunooglobulin superfamily | | |
| IGSF1 | Immunoglobulin superfamily, member 1 isoform 1 | +3.11 | +2.81 |
| IGSF3 | Immunoglobulin superfamily, member 3 isoform 2 | +5.81 | +3.39 |
| | Integrins | | |
| ITGBL1 | Integrin beta-like 1 | −4.38 | No effect |
| ITGB4 | Integrin beta-4 precursor | +3.48 | +7.98 |
| ITG5 | Integrin beta-5 precursor | −2.42 | No effect |
| ITGB6 | Integrin beta-6-precursor | +7.49 | +7.71 |
| ITGB8 | Integrin beta-8 precursor | No effect | +3.90 |
| | Cadherins | | |
| CDH3 | Cadherin-3-precursor (P-cadherin) | +3.99 | +7.47 |
| CDH19 | Cadherin-19-precursor | −4.11 | No effect |
| CDH24 | Cadherin-24-precursor | +2.06 | +2.28 |
| CDH1 | Epithelia-cadherin precursor (E-cadherin) | +9.39 | +21.56 |
| PCDHB1 | Procadherin-beta-1-precursor | No effect | +2.00 |
| PCDHB2 | Procadherin-beta-2-precursor | No effect | +18.74 |
| PCDHB3 | Procadherin-beta-3-precursor | −6.57 | No effect |
| PCDHB4 | Procadherin-beta-4-precursor | −2.62 | −7.81 |
| PCDH11X | Procadherin-11 | +3.18 | +10.15 |
| PCDH18 | Procadherin-18-precursor | −2.49 | No effect |
| PCDH19 | Procadherin-19-precursor | −3.41 | No effect |
| DSG1 | Desmoglein-1-precursor (DG1) | −2.30 | −2.26 |
| DSG2 | Desmoglein-2-precursor | +13.03 | +20.15 |
| DSG3 | Desmoglein-3-precursor | +2.35 | +4.25 |
| DSG4 | Desmoglein-4-precursor | No effect | +10.59 |
| DSC1 | Desmocollin-1-precursor (DG2/DG3) | −7.49 | −5.96 |
| DSC2 | Desmocollin-2-precursor (Desmocollin-3) | +3.71 | +4.68 |
| | Selectins | | |
| SELE | E-selection precursor (Endothelial leukocyte adhesion molecule 1) (ELAM-1) | −2.11 | No effect |

Cytoskeleton Proteins

The cytoskeleton (CSK) is a cellular "scaffolding" or "skeleton" contained within the cytoplasm. The cytoskeleton is present in all cells. It is a dynamic structure that maintains cell shape, often protects the cell, enables cellular motion (using structures such as flagella, cilia and lamellipodia), and plays important roles in both intracellular transport (the movement of vesicles and organelles, for example) and cellular division. The cytoskeleton provides the cell's cytoplasm with structure and shape. Proteins of the cytoskeleton are: (a) actin filaments/microfilaments, (b) intermediate filaments, (c) microtubules, and (d) catenins.

A growing body of evidence suggests that mitochondria use cytoskeletal proteins as tracks for their movement. In turn, mitochondrial morphology and function is regulated via mostly uncharacterized pathways, by the cytoskeleton (Anesti V and Scorrano L, The relationship between mitochondrial shape and function and the cytoskeleton, Biochim et Biophys Acta—Bioenergetics, 1757(5-6):692-699, 2006). The cytoskeleton is subject to damage from UVA radiation, as evidenced by the disappearance of actin microfilament (Provost N, Moreau M, Leturque, Nizard C, UV-A radiation transiently disrupts gap junctional communication in human keratinocytes, American J Physiol Cell Physiol, 284(1):C51-

59, 2003). Sytenol A has shown favorable modulatory effects on Cytoskeleton genes thereby providing improved cell structure and shape.

TABLE 8

Gene expression profile of Cytoskeleton

| Gene | Gene Description | Fold Change | |
|---|---|---|---|
| | | Retinol | Sytenol A |
| Microfilaments | | | |
| ACTN4 | Alpha-actinin-4(F-actin cross-linking protein) | +2.99 | +3.13 |
| ACTN1 | Alpha-actinin-1 (Alpha-actinin cytoskeletal isoform) | +3.11 | +2.70 |
| GSN | Gelsolin precursor (Actin-depolymerizing factor) (ADF) | +3.47 | +3.19 |
| MYO1F | Myosin-lf (Myosin-le) | +6.29 | +3.44 |
| MYL2 | Myosin regulatory light chain 2 | No effect | −2.50 |
| MYO6 | Myosin-VI | No effect | +2.38 |
| MYH14 | Myosin-14 | +3.38 | +5.72 |
| PFN4 | Profilin-4 (Profilin IV) | +4.77 | No effect |
| Intermediate filaments | | | |
| KRT2 | Keratin-2; Cytokeratin-2e (CK 2e) | −8.37 | −3.53 |
| KRT5 | Keratin-5, Cytokeratin-5 (CK-5) | +2.39 | +2.81 |
| KRT7 | Keratin-7; Cytokeratin-7 (CK-7) | +8.75 | +13.75 |
| KRT13 | Keratin-13; Cytokeratin-13 (CK-13) | +14.17 | +16.34 |
| KRT15 | Keratin-15; Cytokeratin-15 (CK-15) | +5.48 | +11.29 |
| KRT19 | Keratin-19; Cytokeratin-19 (CK-19) | +11.27 | +20.67 |
| Microtubules | | | |
| KIF4A | Chromosome-associated kinesin KIF4A | +2.08 | +2.15 |
| KIF2A | Kinesin-like protein KIF2A | −3.62 | No effect |
| KIF1C | Kinesin-like protein KIF1C | +2.47 | +2.03 |
| KIFC2 | Kinesin-like protein KIFC2 | −2.45 | No effect |
| KIF13A | Kinsein-like protein KIF13A | −2.27 | No effect |
| KIF13B | Kinsein-like protein KIF13B | +2.91 | +3.53 |
| KIF17 | Kinesin-like protein KIF17 | +2.18 | +2.44 |

TABLE 8-continued

Gene expression profile of Cytoskeleton

| Gene | Gene Description | Fold Change | |
|---|---|---|---|
| | | Retinol | Sytenol A |
| KIF26A | Kinesin family member 26A | −2.93 | No effect |
| CDK5R1 | Tau protein kinase II 23 kDa subunit (Cyclin-dependent kinase 5 activator 1 precursor (CDK5 activator 1) | +2.17 | +2.66 |
| TTBK1 | Tau-tubulin kinase 1 | −7.99 | No effect |
| TTLL1 | Tubulin polyglutamylase complex subunit 3 (PGs3) | +1.92 | +2.07 |
| LRRC49 | Tubulin polyglutamylase complex subunit 4 (PGs4) | −2.83 | −3.47 |
| TBCEL | Tubulin-specific chaperone cofactor E-like protein (EL) | +2.20 | No effect |
| TUBB2B | Tubulin beta-2B chain | −2.56 | −3.31 |
| MC1R, TUBB3 | Tubulin beta-3-chain (Tubulin beta-III) | +2.99 | +3.23 |
| NGRN, TTLL13 | Tubulin tyrosine ligase-like family, member 13 | +11.61 | +12.65 |
| Catenins | | | |
| CTNNAL1 | Alpha-catenin-related protein (ACRP) | −2.60 | No effect |
| JUP | Catenin gamma (Junction plakoglobin) | +2.43 | +3.83 |

Tight Junctions

Tight junctions are the closely associated areas of two cells whose membranes join together forming a barrier that is virtually impermeable to fluid. Tight junctions are composed of a branching network of sealing protein strands, each strand acting independently from the others. Although more proteins are present, the major types are the claudins and the occluding. These strands associate with different peripheral membrane proteins located on the intracellular side of plasma membrane which anchor the strands to the actin cytoskeleton. Thus, tight junctions join together the cytoskeleton of adjacent cells.

TABLE 9

Gene expression profile of tight junctions

| Gene | Gene Description | Fold Change | |
|---|---|---|---|
| | | Retinol | Sytenol A |
| CLDN3 | Claudin-3 (Clostridium perfringens enterotoxin receptor 2) (CPE-R2) | +5.85 | +10.54 |
| CLDN4 | Claudin-4 (Clostridium perfringens enterotoxin receptor) (CPE-R) | +3.63 | +5.92 |
| CLDN5 | Claudin-5 (Transmembrane protein deleted in VCFS) | −3.66 | No effect |
| CLDN6 | Claudin-6 (Skullin 2) | +2.59 | No effect |
| CLDN7 | Claudin-7 (CLDN-7) | +25.30 | +46.09 |
| CLDN11 | Claudin-11 (Oligodendrocyte-specific protein) | −2.86 | −4.01 |
| CLDN12 | Claudin-12 | +3.73 | +2.00 |
| CLDN16 | Claudin-16 (Paracellin-1) (PCLN-1) | +7.79 | +11.62 |
| C16orf30 | Claudin-like protein 24 | −2.23 | No effect |
| CDH1 | Epithelial-cadherin precursor (E-cadherin) E-Cad/CTF1 | +9.39 | +21.56 |
| F11R | Junctional adhesion molecule 1 (JAM-1) | +5.77 | +8.92 |
| CTNNAL1 | Alpha-catenin-related protein (ACRP) | −2.04 | No effect |
| JUP | Catenin gamma | +2.43 | +3.83 |
| ACTN4 | Alpha-actinin-4(F-actin cross-linking protein) | +2.99 | +3.13 |
| ACTN1 | Alpha-actinin-1 (Alpha-actinin cytoskeletal isoform) | +3.11 | +2.70 |
| AFAP1L2 | Actin filament-associated protein 1-like 2 | +2.84 | +3.84 |
| FLNB | Actin-binding-like protein | +3.89 | +5.87 |

Tight junctions perform three vital functions. First, they hold cells together. Second, they block the movement of integral membrane proteins between the apical and basolateral surfaces of the cell, allowing the specialized functions of each surface (for example receptor-mediated endocytosis at the apical surface and exocytosis at the basolateral surface) to be preserved. This process preserves the transcellular transport. Finally, they prevent the passage of molecules and ions through the space between cells. Consequently, materials must actually enter the cells (by diffusion or active transport) in order to pass through the tissue. This process and associated pathway provide control over what substances are allowed to pass. Tight junctions play this role in maintaining the blood-brain barrier. Sytenol A has shown very favorable modulatory effects on tight junction genes thereby providing improved barrier between two cells.

Growth Factors

"Growth factors" are naturally occurring proteins that cause cells to grow and divide. Cell growth factors include, but are not limited to, epidermal growth factor (EGF), keratinocyte growth factor (KGF), fibroblast growth factor (FGF), insulin-like growth factor (IGF), platelet derived growth factor (PDGF), granulocyte colony-stimulating factor (G-CSF), granulocyte-macrophage colony-stimulating factor (GM-CSF)), tissue growth factor (TGF), and other cell growth factors. EGF is a protein that stimulates epidermal cells to divide. KGF is a growth factor structurally related to fibroblast growth factor. FGF is a growth factor that has been isolated from a variety of cells. It has potent heparin-binding activity and is a potent inducer of DNA synthesis in a variety of normal diploid mammalian cell types from mesoderm and neuroectoderm lineages. It also has chemotactic and mitogenic activities and exists in acidic and basic forms. IGF refers to insulin-like growth factors I and II. Insulin-like growth factors I and II are polypeptides with sequence similarity to insulin and are capable of eliciting similar biological responses to insulin, including mitogenesis, in cell cultures. PDGF is an important mitogen that promotes growth in cell cultures of connective tissue origin. It consists of two different but homologous polypeptides A and B (~30,000 D) linked by disulfide bonds, and plays a role in wound healing. GCSF is a glycoprotein containing internal disulfide bonds that induces the survival, proliferation, and differentiation of neutrophilic granulocyte precursor cells and functionally activates mature blood neutrophils. GMCSF is an acidic glycoprotein with internal disulfide bonds that stimulates the production of neutrophilic granulocytes, macrophages, and mixed granulocyte macrophage colonies from bone marrow cells and can stimulate the formation of eosinophil colonies from fetal liver progenitor cells. It also has some functional activities in mature granulocytes and macrophages. TGFs include many of the bone morphogenetic proteins. TGF alpha (TGFa) is a growth factor that stimulates growth of microvascular endothelial cells. TGF beta (TGFb) stimulates wound healing.

Other "growth factors" include cytokines, which are non-antibody proteins that act as intercellular mediators. They differ from classical hormones in that they are produced by a number of tissue cell types rather than by specialized glands. They generally act locally in a paracrine or autocrine rather than endocrine manner. Cytokines include, but are not limited to, hepatopoietin, erythropoietin and interleukins. Interleukin is the generic name for a group of well-characterized cytokines that are produced by leukocytes and other cell types. Exemplary interleukins include, but are not limited to, IL-1 through 18.

TABLE 10

Gene expression profile of Growth Factors

| | Fold Change | |
|---|---|---|
| Gene Description | Retinal | Sytenol A |
| Fibroblast growth factor-binding protein 1 precursor (FGF-BP1) | +3.51 | +2.69 |
| Heparin-binding EGF-like growth factor precursor (HB-EGF) | +3.89 | +5.09 |
| Insulin-like growth factor-binding protein 6 precursor (IGBP-6) | +5.89 | +4.03 |
| Insulin growth factor-like family member 4 precursor (IGBP-4) | +5.97 | +2.41 |
| Insulin growth factor-like family member 3 precursor (IGBP-3) | −7.11 | −8.67 |
| Fibroblast growth factor receptor 2 precursor (FGFR-2) | +6.50 | +8.93 |
| Fibroblast growth factor 9 (HBGF-9) | −12.36 | −2.34 |
| Fibroblast growth factor 23 precursor (FGF-23) (Tumor-derived hypophosphatemia-inducing factor) | −9.78 | −3.01 |
| Hepatocyte growth factor receptor precursor (HGF receptor) | +26.22 | +3.74 |
| Connective tissue growth factor precursor (Hypertrophic chondrocyte-specific protein 24) | −4.61 | −2.56 |
| Mast/stem cell growth factor receptor precursor (SCFR) (Proto-oncogene tyrosine-protein kinase kit (c-kit) | −3.36 | −2.31 |

Regulatory factors are proteins active in the activation or repression of gene transcription. Regulatory factors include, but are not limited to, human growth hormone and prostaglandin.

Angiogenic factors are proteins that act to vascularize tissue and act in the development of new capillary blood vessels. Angiogenic factors include, but are not limited to, vascular endothelial growth factor (VEGF), fibroblast growth factor (acidic FGF), tissue growth factor (TGF-a), platelet derived growth factor (PDGF). VEGF is a protein that stimulates the growth of new blood vessels. Sytenol A has shown favorable modulatory effects on growth factor genes thereby providing cells to grow and divide when needed.

DNA Repair Enzymes

Poly (ADP-ribose) polymerase (PARP) plays diverse roles in many molecular and cellular processes, including DNA damage detection and repair, chromatin modification, transcription, cell death pathways, insulator function, and mitotic apparatus function. These processes are critical for many physiological and pathophysiological outcomes, including genome maintenance, carcinogenesis, aging, inflammation, and neuronal function. A body of correlative data suggests a link between DNA damage-induced poly(ADP-ribosyl)ation and mammalian longevity. Recent research on PARPs and poly(ADP-ribose) yielded several candidate mechanisms through which poly(ADP-ribosyl)ation might act as a factor that limits the rate of aging. Werner syndrome, a premature-aging disorder, has been linked indirectly to the PARP-family.

TABLE 11

Poly (ADP-ribose) polymerase (PARP) and DNA glycosylases

| | | Fold Change | |
|---|---|---|---|
| Gene | Gene Description | Retinol | Sytenol A |
| PARP2 | Poly (ADP-ribose) polymerase 2 | +2.08 | +1.46 |
| PARP9 | Poly (ADP-ribose) polymerase 9 | +5.92 | +7.74 |
| PARP12 | Poly (ADP-ribose) polymerase 12 | +4.69 | +6.05 |

TABLE 11-continued

Poly (ADP-ribose) polymerase (PARP) and DNA glycosylases

| | | Fold Change | |
|---|---|---|---|
| Gene | Gene Description | Retinol | Sytenol A |
| PARP15 | Poly (ADP-ribose) polymerase 15 | +6.37 | No effect |
| NEIL2 | DNA glycosylase/AP lyase Neil2 | +12.79 | +4.17 |

DNA glycosylases are a family of enzymes involved in base excision repair. Base excision repair is the mechanism by which nucleotide residues in DNA with chemically altered nitrogen bases can be removed and replaced. Sytenol A has shown favorable up-regulatory effects on two key DNA repair genes thereby providing improved amelioration, reduction and/or reversal of skin damage.

Nuclear Factor Kappa-B (NF-kappa-B)

NF-kappa-B is a ubiquitous and well-characterized protein responsible for the regulation of complex phenomena in cells, with a pivotal role in controlling cell signaling under certain physiological and pathological conditions, including stress, UV radiation, cytokines, and viral and bacterial antigens. Among other functions, NF-kappa-B controls the expression of genes encoding the pro-inflammatory cytokines (e.g., IL-1, IL-2, IL-6, TNF-alpha, etc.), chemokines (e.g., IL-8, MIP-1alpha, MCP1, RANTES, eotaxin, etc.), adhesion molecules (e.g., ICAM, VCAM, E-selectin), inducible enzymes (COX-2 and iNOS), growth factors, some of the acute phase proteins, and immune receptors (Nam N H, Mini Rev Med. Chem., 6(8):945-951, 2006). Age-specific NF-B blockade and orthogonal cell cycle interventions revealed that NF-B controls cell cycle exit and gene expression signature of aging in parallel but not sequential pathways. Adler et al was able to identify a conserved network of regulatory pathways underlying mammalian aging and show that NF-B is continually required to enforce many features of aging in a tissue-specific manner (Adler A S, Sinha S, Kawahara T L A, Zhang J Y, Sega E and Chang H Y, Published online before print Nov. 30, 2007, Genes and Development, DOI: 10.1101/gad.1588507).

Sytenol A has shown favorable down-regulatory effects on two key nuclear factor genes thereby providing improved amelioration, reduction and/or reversal of skin damage.

TABLE 12

Gene expression profile of Nuclear factors

| | Fold Change | |
|---|---|---|
| Gene Description | retinol | Sytenol A |
| Nuclear factor Kappa B p105 unit (NF-kappa-B) (DNA-binding factor KBF 1) | −3.62 | −2.01 |
| NF-kappa-B-activating protein | −2.13 | −2.32 |

Sirtuin and Protein Kinase B

Silent information regulator 2 (Sir2) proteins, or sirtuins, are protein deacetylases/mono-ADP-ribosyltransferases found in organisms ranging from bacteria to humans. Sirtuins may be able to control age-related disorders in various organisms and in humans. Several studies show that resveratrol, found in red wine, is a putative agent for slowing down the aging process by modulating sirtuin activity. This mechanism, has, however, been disputed. Resveratrol affects other pathways, including those involving activation of phosphatidylinositol 3-Kinase, inhibition of protein kinase B etc. Regulation of metabolic processes as well as cellular defense mechanisms might ultimately be the key to a possible lifespan-extending role for sirtuins in mammals.

Protein Kinase B (PKB) can block apoptosis, and thereby promote cell survival, PKB has been implicated as a major factor in many types of cancer. PKB was originally identified as the oncogene in retrovirus.

Sytenol A has shown favorable modulatory effects on Sirtuin and protein kinase B genes thereby providing improved amelioration, reduction and/or reversal of skin damage

TABLE 13

Gene expression profile of Sirtuins and Protein Kinase B

| | Fold Change | |
|---|---|---|
| Gene Description | retinol | Sytenol A |
| SIR2-like protein1/NAD-dependent deacetylase sirtuin-1 (hSIRT1) | −1.89 | −1.54 |
| SIR2-like protein2/NAD-dependent deacetylase sirtuin-2 | +1.52 | +1.52 |
| SIR2-like protein7/NAD-dependent deacetylase sirtuin-7 | +1.58 | +2.47 |
| Protein Kinase B (RAC-alpha serine/threonine-protein kinase) (RAC-PK-alpha) | −5.09 | −3.47 |

The foregoing results dramatically demonstrate the marked and unexpected gene modulating or regulatory effect of meroterpenes, particularly bakuchiol. This efficacious response demonstrates and is indicative of the potential for the use of gene manipulating amounts of meroterpenes as a widely applicable medicament for the treatment of any number of human disease or abnormal conditions, not just skin conditions as discussed herein. Indeed, retinol is known as a suitable and efficacious medicament for a wide variety of medical conditions. The results shown above indicate an overall superiority of the meroterpenes to retinal, and without the detrimental aspects and disadvantages of retinal. Thus, for skin and other human, and potentially veterinary, applications, the compositions of the present invention may indeed represent a utopian, or nearly so, medicament.

Example 2

Skin Sensitivity

Given the known sensitivity issues associated with commercial grade bakuchiol, evaluation of the skin sensitivity to the purified bakuchiol was also evaluated. Skin sensitivity was evaluated following the method cited in the reference *Appraisal of the Safety of Chemicals in Food, Drugs and Cosmetics*, published by The Association of Food and Drug Officials of The United States. The method employs nine inductive patching and not the ten cited in the reference under occlusive patch conditions.

Samples were prepared for evaluation by diluting the purified Bakuchiol in corn oil to a 5% concentration, with dilutions freshly prepared on each application day. 0.2 ml or 0.2 g of the diluted test material was dispensed onto the occlusive, hypoallergenic patch and the treated patch applied directly to the skin of the infrascapular regions of the back, to the right or left of the midline of each subject: one hundred and eleven subjects were employed. After application of the patch, each subject was dismissed with instructions not to wet or expose the test area to direct sunlight. The patch was removed by the subject after 24 hours. This procedure was repeated every Monday, Wednesday and Friday for three consecutive weeks until a series of nine consecutive 24 hour exposures had been made. During the test period, the test area on the subjects' backs were observed for evidence of edema or erythema just before applications two through nine and the next test date following application nine. If evidence of a reaction was found, the area of edema and/or erythema was then measured and recorded: edema being estimated by an evaluation of the skin with respect to the contour of the unaffected normal skin. The subjects were then given a 10-14 day rest period after which a challenge or retest dose was applied once to a previously unexposed test site. The retest dose was equivalent to any one of the original nine exposures. Reactions were scored 24 and 48 hours after application. Based on the test results, the 5% dilution in corn oil of the purified bakuchiol was determined to be a NON-PRIMARY IRRITANT and a NON-PRIMARY SENSITIZER according to the reference.

Examples 3A-3C

Formulations for Topical Applications

The following tables set forth various formulations and embodiments of sirtuin-modulating compositions according to the present invention. Following each table is a brief description of the process by which each formulation is made.

Example 3A

Lotion with 1% Sytenol® A

| INCI name | Trade Name/Supplier | % w/w |
| --- | --- | --- |
| Phase A-1 | | |
| Water | Water(demineralized) | 78.70 |
| Disodium EDTA | Versene Na/Dow | 0.10 |
| Glycerine | Emery 916/Cognis | 3.00 |
| Phase A-2 | | |
| Xanthan Gum | Vanzan NF/Vanderbilt | 0.20 |
| Phase B | | |
| Caprylic/Capric Triglyceride | Myritol 318/Cognis | 6.00 |
| Squalane | Fitoderm/Centerchem | 1.00 |
| Cetyl Esters | Crodamol SS/Croda | 1.00 |
| Cetyl Alcohol | Crodacol C-70/Croda | 1.00 |
| Dimethicone | Dow Corning 200, 50 cst/ Dow Corning | 2.00 |
| Glyceryl Stearate, PEG-100 Stearate | Arlacel 165/Uniquema | 3.50 |
| Bakuchiol | Sytenol ® A/Sytheon | 1.00 |
| Phase C | | |
| Hydroxyethyl Acrylate/Sodium Acryloyldimethyl Taurate Copolymer & Squalane & Polysorbate 60 | Simulgel NS/Seppic | 1.50 |
| Phase D | | |
| Phenoxyethanol, Methylparaben, propylparaben, Ethylparaben | Phenonip XB.Clariant | 1.00 |
| Total | | 100.00 |

Procedure:

Combine and intimately mix the ingredients of Phase A-1. Then disperse phase A-2 in A-1 while stirring and heat the mixture to 75° C. Independently, combine the ingredients of Phase B and heat to 75° C. Add Phase B to Phase A with good mixing. Homogenize the mixture at moderate speed, while sequentially adding Phases C and D. Allow the mixture to cool while continuing propeller agitation until a homogeneous mixture is attained.

Example 3B

Anhydrous serum with 2% Sytenol® A

| INCI name | Trade Name/Supplier | % w/w |
| --- | --- | --- |
| Phase A | | |
| Dimethicone, Dimethicol | Dow Corning 1403 Fluid/Dow Corning | 30.00 |
| Cyclomethicone | Dow Corning 344/Dow Corning | 10.00 |
| Phase B | | |
| Squalane | Fitoderm/Centerchem | 3.00 |
| Bakuchiol | Sytenol ® A/Sytheon | 2.00 |
| Phase C | | |
| Cyclomethicone, Polysilicone-11 | Gransil GCM/Grant | 35.00 |
| Cyclomethicone | Dow Corning 344/Dow Corning | 20.00 |
| Total | | 100.00 |

Procedure:

At room temperature, independently combine the ingredients of each Phase and then sequentially combine each Phase in the order listed. A clear translucent serum is attained.

Example 3C

Lotion with 1% Sytenol® A and 2% Salicylic Acid

| INCI name | Trade Name/Supplier | % w/w |
| --- | --- | --- |
| Phase A | | |
| Glyceryl stearate and PEG-100 Stearate | Arlacel 165/Unichema | 1.50 |
| Arachidyl alcohol, Behenyl alcohol, Arachidyl glucoside | Montanov 202/Seppic | 4.00 |
| Dimethyl isosorbide | Arlasolve DMI/Uniqema | 3.00 |
| Isohexadecane | Permethyl 101 A/Presperse | 8.00 |
| Dimethicone | Dow Corning 200, 100 cst/Dow Corning | 2.00 |
| bakuchiol | Sytenol ® A/Sytheon | 1.00 |
| Phase B | | |
| Water | | 64.25 |
| Propylene Glycol | | 2.00 |
| Xanthum gum | Vanzan NF/Vanderbilt | 0.25 |
| Phase C | | |
| Cyclomethicone | Dow Corning 344/Dow Corning | 4.00 |
| Hydroxyethyl Acrylate/Sodium Acryloyldimethyl Taurate Copolymer | Sepinove EMT 10/Seppic | 1.00 |
| Methyl paraben, Propyl paraben, Phenoxyethanol | Phenonip XB/Clariant | 1.00 |
| Phase D | | |
| Pentylene Glycol | Hydrolite-5/Symrise | 3.00 |
| Dimethyl Isosorbide | Arlasolve DMI/Uniqema | 3.00 |
| Salicylic acid | | 2.00 |
| Total | | 100.00 |

Procedure:

Combine the ingredients of Phase A, stir and heat to 70° C. Independently combine the ingredients Phase B, stir and heat to 75° C. Add the prepared Phase A to Phase B with constant mixing. Sequentially add Phases C and D to the mixture while continually homogenizing the mixture at moderate speed and allowing it to cool to 40° C. Thereafter maintain propeller agitation until mixture is homogeneous and cooled to room temperature.

Example 4

Pharmaceutical, Nutritional and Veterinary Formulations

Example 4A

Capsules

Capsules with health-restorative and health promotional benefits:

|   | Ingredient | Amount (g) |
|---|---|---|
| 1 | Bakuchiol | 200 |
| 2 | Microcrystalline Cellulose | 150 |
| 3 | Syloid (Fumed Silicon Dioxide) | 5 |
| 4 | Croscarmellose Sodium | 10 |
| 5 | Stearic Acid | 10 |
|   | TOTAL | 375 |

Procedure:

Individually screen the Syloid and stearic acid through a 30 mesh sieve. Blend the bakuchiol, microcrystalline cellulose, croscarmellose sodium and screened Syloid in a suitable blender for 15 minutes. Then add the screened stearic acid to the mixture in the blender and mix for 5 minutes. Once a homogeneous mixture is attained, fill the mixture into Size 0 Empty Gelatin Capsules (0.1 g wt). The resultant mixture should be sufficient to fill 1000 capsules, providing a target fill weight of 0.375 g (0.475 g for the filled capsule). The filled capsules are then polished.

Example 4B

Capsules

| Ingredient | Amount, g |
|---|---|
| Bakuchiol | 500 |
| Microcrystalline Cellulose | 150 |
| Syloid (Fumed Silicon Dioxide) | 5 |
| Croscarmellose Sodium | 10 |
| Stearic Acid | 10 |
| TOTAL | 675 |

Procedure:

Individually screen the Syloid and stearic acid through a 30 mesh sieve. Blend the bakuchiol, microcrystalline cellulose, croscarmellose sodium and screened Syloid in a suitable blender for 15 minutes. Then add the screened stearic acid to the mixture in the blender and mix for 5 minutes. Once a homogeneous mixture is attained, fill the mixture into Size 00 Empty Gelatin Capsules (0.12 g wt). The resultant mixture should be sufficient to fill 1000 capsules, providing a target fill weight of 0.675 g (0.795 g for the filled capsule). The filled capsules are then polished.

Example-4C

Tablets

| *Psoralea corylifolia* seed extract enriched with bakuchiol (65%) | 379 |
|---|---|
| Sodium ascorbate | 98 |
| Microcrystalline Cellulose | 50 |
| Sodium Saccharin Powder | 2 |
| Compressible Sugar | 100 |
| Stearic Acid | 12 |
| Imitation Orange Flavor | 2 |
| FD&C Yellow #6 Dye | 1 |
| Fumed Silicon Dioxide (#30 mesh) | 6 |
| TOTAL | 650 |

Procedure:

Blend all of the ingredients, other than the stearic acid, in a suitable blender for 15 minutes. Screen the stearic acid through a 30 mesh sieve and add the screened stearic acid to the blender and continue to blend for 5 minutes. The mixture is then divided and compress into tablets with a target weight of 0.650 g. The above formed batch should produce approximately 1000 capsules.

In each of the formulations set forth above, the meroterpene identified could just as readily be substituted with another meroterpene such as bakuchiol, corylifolin, hydroxybakuchiol, etc. Additionally, these formulations are preferably stored and packaged in tinted vessels/containers so as to prevent their exposure to light, especially UV light, until use Similarly, while the foregoing formulations contain many ingredients in addition to the meroterpene and the carrier, namely surfactants, stabilizers, self-tanning agents, antioxidants and the like, these additional ingredients could just as easily have been omitted without compromising the efficacy thereof.

Without further elaboration, it is believed that one skilled in the art, using the preceding description, can utilize the present invention to its fullest extent. Furthermore, while the present invention has been described with respect to aforementioned specific embodiments and examples, it should be appreciated that other embodiments, changes and modifications utilizing the concept of the present invention are possible, and within the skill of one in the art, without departing from the spirit and scope of the invention. The preceding preferred specific embodiments are, therefore, to be construed as merely illustrative, and not limitative of the remainder of the disclosure in any way whatsoever.

I claim:

1. A method of ameliorating or reducing the manifestation or the appearance or depth of lines, wrinkles or creases around the mouth and eyes, between the eyes and on the forehead resulting from chronological aging, hormonal aging, photo-aging and/or actinic aging wherein the method comprises effecting at least a 2 fold up regulation in the expression of one or more genes associated with improving or maintaining the health and integrity of the dermal-epidermal junction (DEJ), at least a 2 fold down regulation in the expression of one or more genes associated with the degradation of the DEJ, or both by administering orally to an individual or topically or intradermally to the aforementioned areas of the skin of an individual manifesting lines, wrinkles or creases a gene manipulatingly effective amount of a composition having a pH of 3.5 to 7 and comprising from 0.5 to 10 wt. percent of a meroterpene and a dermatologically or pharmaceutically acceptable carrier on at least a daily basis until the aforementioned amelioration or reduction is visually noted to the satisfaction of the user, wherein said meroterpene is of the formula

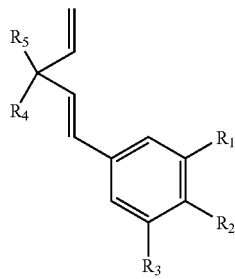

wherein $R_1$, $R_2$, and $R_3$ are each independently selected from the group consisting of H, OH, $OR_6$ or $CH_2R_6$ where $R_6$ is a linear or branched $C_1$ to $C_8$ alkyl; and $R_4$ and $R_8$ are each independently a linear or branched, $C_1$ to $C_{20}$ alkyl or alkenyl group, said meroterpene having a purity of at least 60%.

2. The method of claim 1 wherein gene manipulatingly effective amount is sufficient to induce at least a four-fold up-regulation or down-regulation of at least one gene associated with the health or degradation, respectively, of the DEJ.

3. The method of claim 1 wherein the up-regulation or down-regulation, as appropriate, occurs in at least one of the following genes: LAMA3, LAMC2, ITGA6, ITGB2, ITGB4, ITGB6, ITGB8, COL4A6, COL17A1, AND HS3ST1.

4. The method of claim 1 wherein the composition is administered orally at a rate sufficient to provide a dosing of from about 10 mg to about 500 mg per day, once or twice a day.

5. The method of claim 1 wherein the composition is administered intradermally to the afflicted areas of the skin at a rate sufficient to provide a dosing of 0.1 mg/cm$^2$ to 10 mg/cm$^2$.

6. The method of claim 1 where the composition is administered topically to the afflicted areas of the skin at a rate sufficient to provide a dosing of 0.1 mg/cm$^2$ to 10 mg/cm$^2$.

7. The method of claim 1 where the composition is administered topically to the afflicted areas of the skin at a rate sufficient to provide a dosing of 1 mg/cm$^2$ to 2 mg/cm$^2$.

8. The method of claim 1 wherein the meroterpene is present in the composition in an amount of from 1 to 5 weight percent.

9. The method of claim 1 wherein the meroterpene is selected from bakuchiol, hydroxy bakuchiol, and corylifolin.

10. The method of claim 9 wherein the meroterpene is substantially free of coumarins.

11. The method of claim 1 wherein the meroterpene is selected from bakuchiol, hydroxy bakuchiol, and corylifolin and has a purity of at least 95%.

12. The method of claim 9 wherein the meroterpene is substantially free of coumarins.

13. The method of claim 1 wherein the meroterpene is bakuchiol.

14. The method of claim 9 wherein the meroterpene is bakuchiol.

15. The method of claim 9 wherein the meroterpene is bakuchiol.

16. The method of claim 1 wherein the composition is applied as a topical composition and further includes at least one of a moisturizer, a skin softener, a cosmetic, a skin care active, and a sunscreen.

* * * * *